(12) United States Patent
Sackstein et al.

(10) Patent No.: US 11,517,580 B2
(45) Date of Patent: Dec. 6, 2022

(54) FUCOSYLTRANSFERASE SPECIFIC INHIBITION USING FUCOSE MIMETICS

(71) Applicants: The Florida International University Board of Trustees, Miami, FL (US); University of Florence, Florence (IT)

(72) Inventors: Robert Sackstein, Miami, FL (US); Barbara Richichi, Florence (IT); Kyle Martin, Miami, FL (US)

(73) Assignees: THE FLORIDA INTERNATIONAL UNIVERSITY BOARD OF TRUSTEES, Miami, FL (US); UNIVERSITY OF FLORENCE, Florence (IT)

( * ) Notice: Subject to any disclaimer, the term of this patent is extended or adjusted under 35 U.S.C. 154(b) by 0 days.

(21) Appl. No.: 17/136,839

(22) Filed: Dec. 29, 2020

(65) Prior Publication Data

US 2022/0211734 A1 Jul. 7, 2022

(51) Int. Cl.
*A61K 31/7042* (2006.01)
(52) U.S. Cl.
CPC .................... *A61K 31/7042* (2013.01)
(58) Field of Classification Search
None
See application file for complete search history.

(56) References Cited

PUBLICATIONS

Khodair, Synthesis 2004, No. 1, pp. 0053-0058. (Year: 2004).*
Vedantu, Questions & Answers > CBSE >Chemistry > Grade 12 > Structural Isomerism of Organic Compounds, https://www.vedantu.com/question-answer/which-of-the-following-compounds-can-exhibit-class-12-chemistry-cbse-5fa0f26e13ca034d15996cf3, internet article downloaded Jan. 27, 2022. (Year: 2022).*
Goyard, D., et al. ,"Multivalent Glycomimetics with Affinity and Selectivity toward Fucose-Binding Receptors from Emerging Pathogens." Bioconjugate Chemistry, 2018, 29: 83-88.
Richichi, B., et al., "Synthesis of a selective inhibitor of a fucose binding bacterial lectin from Burkholderia ambifaria." Organic & Biomolecular Chemistry, 2013, 11:4086-4094.
Richichi, B., et al., "Sialylexoenitols as precursors for new analogues of sialidase inhibitors." Pure appl. Chem., 2013, 85(9): 183-1811.
Richichi, B., et al., "Stereoselective synthesis and sialidase inhibition properties of KDO-based glycosyloxathiins." ARKIVOC, 2014, 3: 65-79.

* cited by examiner

*Primary Examiner* — Layla D Berry
(74) *Attorney, Agent, or Firm* — Saliwanchik, Lloyd & Eisenschenk

(57) ABSTRACT

Provided are compositions and methods for specific fucosyltransferase inhibition for treatment of a variety of diseases. The compositions of the invention comprise a glycomimetic of L-Fucose that selectively inhibits the generation of sialyl Lewis X by FTVI and FTVII but has no effect on the generation of Lewis X by FTIX.

12 Claims, 7 Drawing Sheets

| Cell Type (Structure) | Comparison of Treatments | P value | Cell Type (Structure) | Treatment | P value |
|---|---|---|---|---|---|
| RPMI sLe^x | FTVII vs 1:1 | P < 0.01 | MSC sLe^x | FTVII vs 1:1 | P < 0.05 |
|  | FTVII vs 1:2 | P < 0.01 |  | FTVII vs 1:2 | P < 0.05 |
|  | FTVII vs 1:2 Pre | P < 0.01 |  | FTVII vs 1:2 Pre | P < 0.01 |
| RPMI Le^x | FTIX vs 1:1 | P > 0.05 | MSC Le^x | FTIX vs 1:1 | P > 0.05 |
|  | FTIX vs 1:2 | P > 0.05 |  | FTIX vs 1:2 | P > 0.05 |
|  | FTIX vs 1:2 Pre | P < 0.05 |  | FTIX vs 1:2 Pre | P > 0.05 |
| RPMI sLe^x | FTVI vs 1:1 | P < 0.05 | MSC sLe^x | FTVI vs 1:1 | P < 0.05 |
|  | FTVI vs 1:2 | P < 0.01 |  | FTVI vs 1:2 | P < 0.01 |
|  | FTVI vs 1:2 Pre | P < 0.01 |  | FTVI vs 1:2 Pre | P < 0.01 |
| RPMI Le^x | FTVI vs 1:1 | P < 0.05 | MSC Le^x | FTVI vs 1:1 | P > 0.05 |
|  | FTVI vs 1:2 | P < 0.01 |  | FTVI vs 1:2 | P < 0.01 |
|  | FTVI vs 1:2 Pre | P < 0.01 |  | FTVI vs 1:2 Pre | P < 0.01 |

FIG. 3

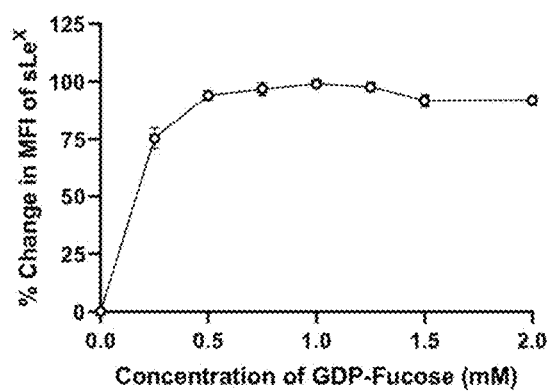

FIG. 4A

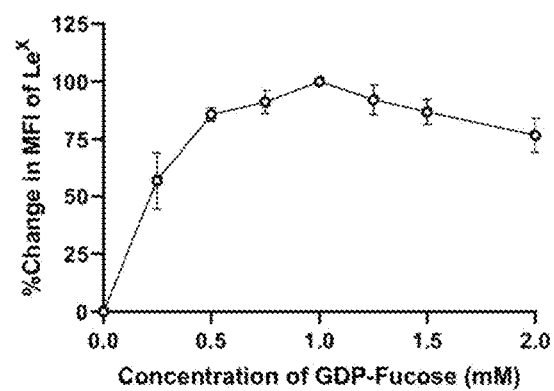

FIG. 4B

FUCOSYLTRANSFERASE SPECIFIC INHIBITION USING FUCOSE MIMETICS

GOVERNMENT SUPPORT

This invention was made with government support under Grant No. CA225730, awarded by The National Institutes of Health. The government has certain rights in the invention.

BACKGROUND OF THE INVENTION

The capacity to custom-modify cellular glycosylation without genetic manipulation of target cells holds great implications for therapeutics for the treatment of a variety of conditions.

Fucosyltransferases (FTs) are key enzymes involved in the biosynthesis of fucosylated glycoconjugates on the cell surface. These enzymes catalyze the transfer of L-Fucose as a nucleotide-activated donor substrate GDP-Fucose (GDP-Fuc) to structurally diverse acceptors.

Among the family of FTs, there are α-1,3-FTs that specifically modify terminal lactosaminyl glycans, the last step in biosynthesis of Lewis X antigens, i.e., "Lewis X" ($Le^X$; CD15) and "sialyl Lewis X" ($sLe^x$; CD15s). The α-1,3-FTs are responsible for installing terminal L-fucose residues on Type 2 lactosamines located at the termini of glycan chains as "neutral type 2 lactosamines", i.e., Gal-β(1,4)-GlcNAc-α-1-R, 'LacNAc', the precursor of $Le^X$ or as "sialylated Type 2 lactosamines", i.e., NeuAc-α(2,3)-Gal-β(1,4)-GlcNAc-α-1-R, sLacNAc', the precursor of $sLe^X$.

In humans there are six α-1,3-FTs. The principal α-1,3-FTs that mediate $sLe^X$ creation are fucosyltransferase VI (FTVI) and fucosyltransferase VII (FTVII), with fucosyltransferase IX (FTIX) dominating $Le^X$ synthesis. Notably, FTVII makes only $sLe^X$, FTIX makes only $Le^X$ and FTVI makes both $sLe^X$ and $Le^X$. The tetrasaccharide $sLe^X$ is the canonical binding determinant for the selectins (CD62E, CD62L, CD62P), a family of $Ca^{++}$-dependent lectins that direct critical cell-cell adhesive interactions.

Thus, Type 2 lactosaminyl glycan fucosylation mediated by α-1,3-FTs plays a crucial role in a variety of biologic events including leukocyte trafficking, human fertilization, metastasis, and immune cell differentiation. Upregulated α-1,3-FTs activity resulting in the overexpression of $Le^X$ and $sLe^X$ determinants is etiologic in several human diseases including cancer and autoimmune conditions, e.g., rheumatoid arthritis, Crohn's disease, and diabetes.

BRIEF SUMMARY OF THE INVENTION

The subject invention provides methods and compositions for selective inhibition of fucosyltransferases (FTs) based on glycomimetics of L-Fucose that markedly inhibit the creation of $sLe^X$ by FTVI and FTVII, but have no effect on the creation of $Le^X$ by FTIX.

The compounds of the invention can be used in methods to treat a variety of conditions that involve cell surface glycans, including, but not limited to, acute and chronic inflammatory conditions, congenital/genetic diseases, infectious diseases, autoimmune diseases, toxic injuries, cancer, trauma, and acute and chronic vascular conditions.

Advantageously, the fucose mimetic compounds of the invention enable an effective and selective inhibition of fucosyltransferases and can be used for tailored treatment of glycan-related conditions. Specifically, the compounds of the invention facilitate the custom-modification of cell surface glycans by inhibiting the generation of $sLe^X$ by FTVI and FTVII with no effect on the generation of $Le^X$ by FTIX. Thus, the compounds and methods of the invention enable the selective suppression of $sLe^X$ display on cells in a subject, where the selective suppression of $sLe^X$ on cells is used in the treatment of conditions involving, for example, leukocyte trafficking, fertilization, metastasis, and immune cell differentiation.

Also provided are methods for the stereoselective synthesis of fucose mimetic and analog compounds by means of a Diels-Alder cycloaddition.

BRIEF DESCRIPTION OF THE DRAWINGS

FIG. 3 shows the P value table for FIGS. 2A, 2B, and 2C containing P values for all reactions in FIGS. 2A, 2B, and 2C. Statistical analysis was performed using one-way AOPVA followed by Dunnett's multiple comparisons test where appropriate. For all experiments n=3.

FIG. 4A shows the percent change of mean fluorescence intensity of $sLe^X$ after exofucosylation of RPMI-8402 cells using FTVI. FIG. 4B shows the percent change of mean fluorescence intensity of $Le^X$ after exofucosylation of RPMI-8402 cells using FTVI.

DETAILED DESCRIPTION OF THE INVENTION

Figure 1A:
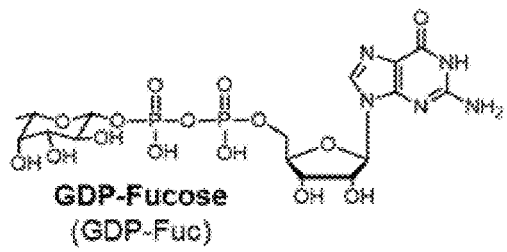
FIG. 1A shows the structures of GDP-Fuc and mimetic 1.

The subject invention provides methods and compositions for selective inhibition of fucosyltransferases. Advantageously, the methods and compositions of the subject invention provide efficient and selective inhibition of disease-relevant fucosyltransferases. Also provided are methods for screening mimetics for use as selective fucosyltransferase inhibitors.

To achieve glycoengineering of cell surface glycans and treat conditions that are affected by cell surface glycans, the instant invention provides non-toxic, selective inhibitors that possess exquisite specificity for target Golgi glycosyltransferase(s). Importantly, the inhibitors of the instant invention are selective solely for the target glycosyltransferase and have no effect on other (non-target) glycosyltransferases, thereby achieving the selective generation of desired glycan product(s).

In some embodiments, the glycosyltransferase inhibitors of the subject invention target fucosyltransferases. In preferred embodiments, the glycosyltransferase inhibitors of the invention target fucosyltransferases that synthesize α-1,3-fucosylated glycans. For example, in certain embodiments, the inhibitors of the invention target fucosyltransferases VI and VII. In further embodiments, the glycosyltransferase inhibitors of the invention target additional α-1,3-fucosyltransferases including, but not limited to, fucosyltransferases III, IV, V, IX, X and XI.

In preferred embodiments, the glycosyltransferase inhibitors of the subject invention target fucosyltransferases that synthesize sialyl Lewis X. In further preferred embodiments, the glycosyltransferase inhibitors of the invention do not target fucosyltransferases that synthesize non-sialyl Lewis X lectins, including but not limited to, Lewis X and other non-Lewis X lectins. For example, the glycosyltransferase inhibitors of the invention do not reduce the levels of Lewis X.

In some embodiments, the glycosyltransferase inhibitors of the invention are glycomimetics of L-fucose including, but are not limited to, fucose mimetics, structural fucose analogs and functional fucose analogs. The fucose mimetic compounds, and structural and/or functional analogs can be monovalent or multivalent. In some embodiments, multivalent constructs comprise covalently or noncovalently linked fucose mimetics of the invention. Specifically, the multivalent constructs can consist on, be associated with and/or be present within organic/inorganic-based micro- or nanoparticles of different shape (i.e. sphere, rods, start, cubic, diamond, amorphous) and size (i.e. nm, μm). The micro- or nanoparticles include but are not limited to, dendrimers, dendrons, polymeric nanomaterials and carbohydrate- or peptide/proteins or lipids- or nucleotide/nucleoside-based nanoparticles, liposomes, micelles, and gold or silver or silica or polyesters (i.e., polylactide, polycaprolactone and poly(lactic-co-glycolic acid)) nanoparticles, and viral or carbon-based (i.e., carbon nanotubes, graphene, carbon dots), external-stimuli responsive hydrogels.

In some embodiments, the fucose mimetic compounds of the invention have Structure A (Structure A)

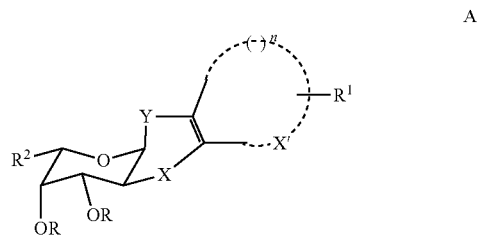

wherein the dotted line in Structure A can be, but is not limited to, an aliphatic, an aromatic, a heteroaliphatic, or a heteroaromatic ring and is substituted with at least one R$^1$, wherein the ring can be substituted with any number of R$^1$ substituents up to the maximum number permitted by the structure of the ring, and n is an integer selected from the group consisting of 2, 3, 4, 5, 6, 7 and 8. At each occurrence R is hydrogen or comprises a protecting group. The protecting group can form an ester with the adjacent oxygen atom. The protecting group can also be a functional group which responds to external/internal stimuli (e.g., pH, enzyme, light, oxidation, or temperature dependent stimuli). For example, the functional group can be a group that targets the fucose mimetic compound to a specific cell organelle. In some embodiments, the functional group is a Golgi-targeting moiety. The Golgi targeting modules can be, but are not limited to, (D/L)-cysteine, mono-, di-, tri-thiols containing modules, fat acid modules with saturated and unsaturated alkyl chains, natural ceramide and related analogues, SNAP-Tag substrate, Halo-Tag substrate, sulphonamide derivatives, or myristoyl-Gly-Cys module. In some embodiments, the Golgi-targeting module can be covalently conjugated to R, $R^1$, $R^2$, and/or R". The covalent conjugation can be performed with or without an alkyl/aryl spacer which can be linked through a bond that is cleavable by a specific stimulus, e.g., pH, enzyme, light, and/or temperature or through a stable bond. At each occurrence, R can be, but is not limited to, hydrogen, hydroxyl group, alkoxy group, amino group, thiol group, sulfoxide group, sulfone group, sulfonamide group, sulphate group, sulfonate group, keto group, formyl group, carboxylic group, azido group, (mono-, di, tri-) phosphate group, (mono-, di-, tri-) phosphonate group, ester group, amide group, or anhydride group, wherein each group can be unsubstituted or substituted with an alkyl or aryl group. At each occurrence $R^1$ can be, but is not limited to, hydrogen, hydroxyl group, alkoxy group, amino group, thiol group, sulfoxide group, sulfone group, sulfonamide group, sulphate group, sulfonate group, keto group, formyl group, carboxylic group, azido group, (mono-, di, tri-) phosphate group, (mono-, di-, tri-) phosphonate group, ester group, amide group, or anhydride group, wherein each group can be unsubstituted or substituted with an alkyl or aryl group. Further, at each occurrence $R^1$ can be, but is not limited to, an aryl group selected from an aromatic, heteroaromatic ring (as fused and not fused ring), or an alkyl group, selected from a saturated or unsaturated aliphatic or heteroaliphatic ring (as fused and not fused ring), an alkyl chain or heteroalkyl chain. The alkyl chain or heteroalkyl chain can be straight-chained or branched, saturated or unsaturated. The alky group or aryl group can be substituted with at least one group selected from an aryl group, hydroxyl group, alkoxy group, amino group, thiol group, sulfoxide group, sulfone group, sulfonamide group, sulphate group, sulfonate group, keto group, formyl group, or a carboxylic or an azido group, or a (mono-, di-, tri-) phosphate group, (mono-, di-, tri-) phosphonate group or an ester group, amide group, or anhydride group. X and Y can be, but are not limited to, $CH_2$, S, S=O, $SO_2$, O or NH; X' can be C, S, S=O, $SO_2$, O, or N, wherein X' can be present in all positions of the dotted line. $R^2$ can be $CH_2R''$, $CH_2OR''$, $CH_2N(R'')_2$, or $CH_2SR''$; R" can be hydrogen, hydroxyl group, alkoxy group, amino group, thiol group, sulfoxide group, sulfone group, sulfonamide group, sulphate group, sulfonate group, keto group, formyl group, carboxyl group, azido group, a (mono-, di-, tri-) phosphate group, (mono-, di-, tri-) phosphonate group. R" can also be an aryl group selected from an aromatic or an heteroaromatic, or alkyl group, selected from a saturated or unsaturated aliphatic or heteroaliphatic ring or an alkyl chain or heteroalkyl chain. The alkyl chain or the heteroalkyl chain can be straight-chained or branched, saturated or unsaturated. The alkyl group or aryl group can be substituted with at least one group selected from aryl group, hydroxyl group, alkoxy group, amino group, thiol group, sulfoxide group, sulfone group, sulfonamide group, sulphate group, sulfonate group, keto group, formyl group, azido group, or a carboxylic group or a (mono-, di-, tri-) phosphate group, (mono-, di-, tri-) phosphonate group. In some embodiments, X' is present in more than one position of the dotted line. In some embodiments, n is selected from the group consisting of 2, 3, 4, 5, and 6. In other embodiments, Y is O and X is S.

In further embodiments, the fucose mimetic compounds of the invention have Structure A'

(Structure A')

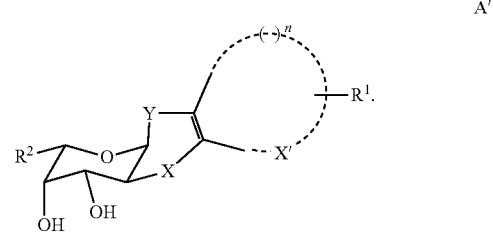

In some embodiments, the dotted line of the fucose mimetic compounds according to Structure A is an aromatic or heteroaromatic five-membered ring and the compounds have Structure B (Structure B)

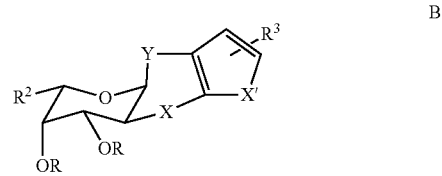

wherein the five-membered ring is substituted with at least one $R^3$, wherein the ring can be substituted with any number of $R^3$ substituents up to the maximum number permitted by the structure of the five-membered ring. At each occurrence $R^3$ can be, but is not limited to, hydrogen, hydroxyl group, alkoxy group, amino group, thiol group, sulfoxide group, sulfone group, sulfonamide group, sulphate group, sulfonate group, keto group, formyl group, azido group, or a carboxylic group, (mono-, di-, tri-) phosphate group, (mono-, di-, tri-) phosphonate group, ester group, amide group or anhydride group, an aryl group (including mono-, di-, tri-, tetrasubstituted derivatives) selected from an aromatic or heteroaromatic, or an alkyl group selected from a saturated or unsaturated aliphatic or heteroaliphatic ring (as fused and not fused ring), or an alkyl chain or heteroalkyl chain. The alkyl chains can be straight-chained or branched, saturated or unsaturated. The alkyl group or aryl group can be substituted with at least one group selected from an aryl group, hydroxyl group, alkoxy group, amino group, thiol group, sulfoxide group, sulfone group, sulfonamide group, sulphate group, sulfonate group, keto group, formyl group, a carboxylic group, azido group, or a (mono-, di-, tri-) phosphate group, (mono-, di-, tri-) phosphonate group, or an ester group, amide group, or anhydride group. In further embodiments, X' can be C, S, S=O, $SO_2$, O, or N and can be present in all positions of the five-membered ring. In some embodiments, X' is present in more than one position of the five-membered ring. At each occurrence R is hydrogen or comprises a protecting group. The protecting group can form an ester with the adjacent oxygen atom. The protecting group can also be a functional group which responds to external/internal stimuli (e.g., pH, enzyme, light, oxidation, or temperature dependent stimuli). For example, the functional group can be a group that targets the fucose mimetic compound to a specific cell organelle. In some embodiments, the functional group is a Golgi-targeting moiety. The Golgi targeting modules can be, but are not limited to, (D/L)-cysteine, mono-, di-, tri-thiols containing modules, fat acid modules with saturated and unsaturated alkyl chains, natural ceramide and related analogues, SNAP-Tag substrate, Halo-Tag substrate, sulphonamide derivatives, or myristoyl-Gly-Cys module. At each occurrence, R can be, but is not limited to, hydrogen, hydroxyl group, alkoxy group, amino group, thiol group, sulfoxide group, sulfone group, sulfonamide group, sulphate group, sulfonate group, keto group, formyl group, carboxylic group, azido group, (mono-, di, tri-) phosphate group, (mono-, di-, tri-) phosphonate group, ester group, amide group, or anhydride group, wherein each group can be unsubstituted or substituted with an alkyl or aryl group. In some embodiments, a Golgi-targeting module can be covalently conjugated to R, $R^2$, R" and/or $R^3$. The covalent conjugation can be performed with or without an alkyl/aryl spacer which can be linked through a bond that is cleavable by a specific stimulus, e.g., pH, enzyme, light, and/or temperature or through a stable bond.

In further embodiment, the fucose mimetic compounds of the invention have Structure B'

(Structure B')

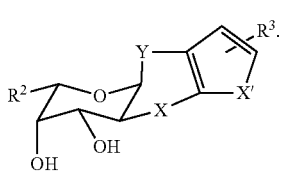

In some embodiments, the dotted line of the fucose mimetic compounds according to Structure A is an aromatic or heteroaromatic six-membered ring and the compounds have Structure C (Structure C)

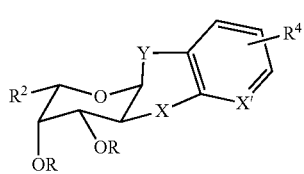

wherein the six-membered ring is substituted with at least one $R^4$, wherein the ring can be substituted with any number of $R^4$ substituents up to the maximum number permitted by the structure of the six-membered ring. At each occurrence $R^4$ can be, but is not limited to, hydrogen, a hydroxyl group, alkoxy group, amino group, thiol group, sulfoxide group, sulfone group, sulfonamide group, sulphate group, sulfonate group, keto group, formyl group, carboxylic group, azido group, (mono-, di-, tri-) phosphate group, (mono-, di-, tri-) phosphonate group, an ester group, amide group, or anhydride group, wherein each group can be unsubstituted or substituted with an alkyl or aryl group. Further, at each occurrence $R^4$ can be, but is not limited to, an aryl group (at the ortho-, meta-, or para-positions including mono-, di-, tri- and tetra-substituted derivatives) selected from an aromatic or heteroaromatic or an alkyl group selected from a saturated or unsaturated aliphatic or an heteroaliphatic ring (as fused and not fused ring), or alkyl chain or heteroalkyl chain. The alkyl chain can be straight-chained or branched, saturated or unsaturated. The alkyl group or aryl group can be substituted with at least one group selected from an aryl group, hydroxyl group, alkoxy group, amino group, thiol group, sulfoxide group, sulfone group, sulfonamide group, sulphate group, sulfonate group, keto group, formyl group, carboxylic group, azido group, (mono-, di-, tri-) phosphate group, (mono-, di-, tri-) phosphonate group, ester group, amide group, or anhydride group. In further embodiments, X' can be C, S, S=O, $SO_2$, O, or N and can be present in all positions of the six-membered ring. In some embodiments, X' is present in more than one position of the six-membered ring. At each occurrence R is hydrogen or comprises a protecting group. The protecting group can form an ester with the adjacent oxygen atom. The protecting group can also be a functional group which responds to external/internal stimuli (e.g., pH, enzyme, light, oxidation, or temperature dependent stimuli). For example, the functional group can be a group that targets the fucose mimetic compound to a specific cell organelle. In some embodiments, the functional group is a Golgi-targeting moiety. The Golgi targeting modules can be, but are not limited to, (D/L)-cysteine, mono-, di-, tri-thiols containing modules, fat acid modules with saturated and unsaturated alkyl chains, natural ceramide and related analogues, SNAP-Tag substrate, Halo-Tag substrate, sulphonamide derivatives, or myristoyl-Gly-Cys module. At each occurrence, R can be, but is not limited to, hydrogen, hydroxyl group, alkoxy group, amino group, thiol group, sulfoxide group, sulfone group, sulfonamide group, sulphate group, sulfonate group, keto group, formyl group, carboxylic group, azido group, (mono-, di, tri-) phosphate group, (mono-, di-, tri-) phosphonate group, ester group, amide group, or anhydride group, wherein each group can be unsubstituted or substituted with an alkyl or aryl group. In some embodiments, a Golgi-targeting module can be covalently conjugated to R, $R^2$, R" and/or $R^4$. The covalent conjugation can be performed with or without an alkyl/aryl spacer which can be linked through a bond that is cleavable by a specific stimulus, e.g., pH, enzyme, light, and/or temperature or through a stable bond.

In further embodiment, the fucose mimetic compounds of the invention have Structure C'

(Structure C')

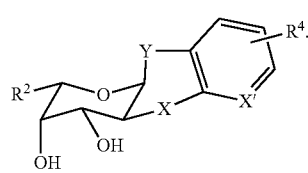

In some embodiments, the fucose mimetic compounds of the invention comprise an aliphatic or hetero-aliphatic ring and the compounds have Structure D (Structure D)

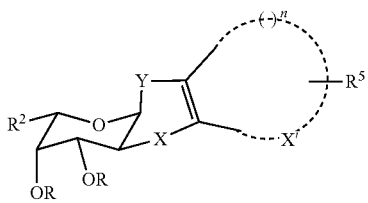

wherein the dotted line in Structure D can be an aliphatic or heteroaliphatic ring and is substituted with at least one $R^5$, wherein the ring can be substituted with any number of $R^5$ substituents up to the maximum number permitted by the structure of the ring, and n is an integer selected from the group consisting of 2, 3, 4, 5, 6, 7 and 8. X and Y can be, but are not limited to, $CH_2$, S, S=O, $SO_2$, O or NH; X' can be C, S, S=O, $SO_2$, O, or N, wherein X' can be present in all positions of the dotted line and wherein in some embodiments X' is present in more than one position of the dotted line. $R^2$ can be, but is not limited to, $CH_2R''$, $CH_2OR''$, $CH_2N(R'')_2$, or $CH_2SR''$. R'' can be hydrogen, hydroxyl group, alkoxy group amino group, thiol group, sulfoxide group, sulfone group, sulfonamide group, sulphate group, sulfonate group, keto group, formyl group, carboxylic group, azido group, (mono-, di- or tri-) phosphate, (mono-, di-, tri-) phosphonate group, aryl group selected from an aryl or an heteroaryl or an alkyl group selected from an saturated or unsaturated aliphatic or heteroaliphatic ring or alkyl chain or heteroalkyl chain. The alkyl chain can be straight-chained or branched, saturated or unsaturated. The alkyl group or aryl group can be substituted with at least one group selected from an aryl group, a hydroxyl group, alkoxy group, amino group, thiol group, sulfoxide group, sulfone group, sulfonamide group, sulphate group, sulfonate group, keto group, formyl group, carboxylic group, azido group, (mono-, di-, tri-) phosphate group, (mono-, di-, tri-) phosphonate group. At each occurrence R is hydrogen or comprises a protecting group. The protecting group can form an ester with the adjacent oxygen atom. The protecting group can also be a functional group which responds to external/internal stimuli (e.g., pH, enzyme, light, oxidation, or temperature dependent stimuli). For example, the functional group can be a group that targets the fucose mimetic compound to a specific cell organelle. In some embodiments, the functional group is a Golgi-targeting moiety. The Golgi targeting modules can be, but are not limited to, (D/L)-cysteine, mono-, di-, tri-thiols containing modules, fat acid modules with saturated and unsaturated alkyl chains, natural ceramide and related analogues, SNAP-Tag substrate, Halo-Tag substrate, sulphonamide derivatives, or myristoyl-Gly-Cys module. In some embodiments, the Golgi-targeting module can be covalently conjugated to R, $R^2$, R'', and/or $R^5$. The covalent conjugation can be performed with or without an alkyl/aryl spacer which can be linked through a bond that is cleavable by a specific stimulus, e.g., pH, enzyme, light, and/or temperature or through a stable bond. At each occurrence, R can be, but is not limited to, hydrogen, hydroxyl group, alkoxy group, amino group, thiol group, sulfoxide group, sulfone group, sulfonamide group, sulphate group, sulfonate group, keto group, formyl group, carboxylic group, azido group, (mono-, di, tri-) phosphate group, (mono-, di-, tri-) phosphonate group, ester group, amide group, or anhydride group, wherein each group can be unsubstituted or substituted with an alkyl or aryl group At each occurrence $R^5$ can be, but is not limited to, hydrogen, hydroxyl group, alkoxy group, amino group, thiol group, sulfoxide group, sulfone group, sulfonamide group, sulphate group, sulfonate group, keto group, formyl group, a carboxylic group, azido group, (mono-, di-, tri-) phosphate group, (mono-, di-, tri-) phosphonate group, ester group, amide group, anhydride derivative, an aryl group (at the different positions of the aliphatic or heteroaliphatic ring including from mono-, up to fully substituted derivatives according with the value of n) selected from an aromatic or heteroaromatic or an alkyl group selected from a saturated or unsaturated aliphatic or heteroaliphatic ring (as fused and not fused ring), or alkyl chain or heteroalkyl chain. The alkyl chain can be straight-chained or branched, saturated or unsaturated. The alkyl group or aryl group can be substituted with at least one group selected from an aryl group, hydroxyl group, alkoxy group, amino group, thiol group, sulfoxide group, sulfone group, sulfonamide group, sulphate group, sulfonate group, keto group, formyl group, carboxylic group, azido group, (mono-, di-, tri-) phosphate group, (mono-, di-, tri-) phosphonate group, ester group, amide group, or anhydride group. In some embodiments, n is selected from the group consisting of 2, 3, 4, 5, and 6.

In some embodiments, the fucose mimetic compounds of the invention comprise an aliphatic or hetero-aliphatic ring and the compounds have Structure D'

(Structure D')

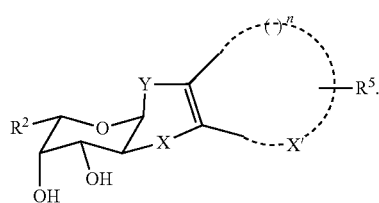

In some embodiments, the fucose mimetic compounds of the invention are bicylic and have Structure E (Structure E)

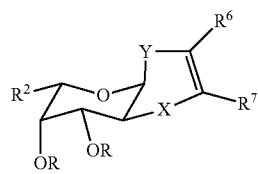

wherein X and Y can be, but not limited to, $CH_2$, S, S=O, $SO_2$, O or NH; $R^2$ can be $CH_2R''$, $CH_2OR''$, $CH_2N(R'')_2$, or $CH_2SR''$. At each occurrence R is hydrogen or comprises a protecting group. The protecting group can form an ester with the adjacent oxygen atom. The protecting group can also be a functional group which responds to external/internal stimuli (e.g., pH, enzyme, light, oxidation, or temperature dependent stimuli). For example, the functional group can be a group that targets the fucose mimetic compound to a specific cell organelle. In some embodiments, the functional group is a Golgi-targeting moiety. The Golgi targeting modules can be, but are not limited to, (D/L)-cysteine, mono-, di-, tri-thiols containing modules, fat acid modules with saturated and unsaturated alkyl chains, natural ceramide and related analogues, SNAP-Tag substrate, Halo-Tag substrate, sulphonamide derivatives, or myristoyl-Gly-Cys module. In some embodiments, the Golgi-targeting module can be covalently conjugated to R, $R^2$, R", $R^6$ and/or $R^7$. The covalent conjugation can be performed with or without an alkyl/aryl spacer which can be linked through a bond that is cleavable by a specific stimulus, e.g., pH, enzyme, light, and/or temperature or through a stable bond. At each occurrence, R can be, but is not limited to, hydrogen, hydroxyl group, alkoxy group, amino group, thiol group, sulfoxide group, sulfone group, sulfonamide group, sulphate group, sulfonate group, keto group, formyl group, carboxylic group, azido group, (mono-, di, tri-) phosphate group, (mono-, di-, tri-) phosphonate group, ester group, amide group, or anhydride group, wherein each group can be unsubstituted or substituted with an alkyl or aryl group. R" can be hydrogen, hydroxyl group, amino group, thiol group, sulfoxide group, sulfone group, sulfonamide group, sulphate group, sulfonate group, keto group, formyl group, carboxyl group, azido group, a (mono-, di- or tri-) phosphate group. a (mono-, di-, tri-) phosphonate group or an aryl group selected from an aromatic or an heteroaromatic, or an alkyl group which consists on a saturated or unsaturated aliphatic or an heteroaliphatic ring or alkyl chain or heteroalkyl chain. The alkyl chain can be straight-chained or branched, saturated or unsaturated. The alkyl group or aryl group can be substituted with at least one group selected from a hydroxyl group, alkoxy group, amino group, thiol group, sulfoxide group, sulfone group, sulfonamide group, sulphate group, sulfonate group, keto group, formyl group, carboxyl group, azido group, (mono-, di-, tri-) phosphate group, or a (mono-, di-, tri-) phosphonate group. X and Y can be, but are not limited to, $CH_2$, S, S=O, $SO_2$, O or NH. $R^6$ and $R^7$ can each independently be, but are not limited to, hydrogen, or a hydroxyl group, amino group, thiol group, sulfoxide group, sulfone group, sulfonamide group, sulphate group, sulfonate group, keto group, formyl group, carboxylic group, azido group, (mono-, di-, tri-) phosphate group, (mono-, di-, tri-) phosphonate group, ester group, amide group, or anhydride group, an aryl group selected from an aromatic or heteroaromatic, or an alkyl group selected from a saturated or unsaturated aliphatic or heteroaliphatic ring, a polycyclic aliphatic, alkyl, or heteroalkyl chain. The alkyl chain can be straight-chained or branched, saturated or unsaturated. The alkyl group or aryl group can be substituted with at least one group selected from an aryl group, hydroxyl group, alkoxy group, halo group, amino group, thiol group, sulfoxide group, sulfone group, sulfonamide group, sulphate group, sulfonate group, keto group, formyl group, carboxylic group, azido group, (mono-, di-, tri-) phosphate group, ester group, amide group, or anhydride group. In some embodiments, Y is O and X is S.

In some embodiments, the fucose mimetic compounds of the invention have Structure E'

(Structure E')

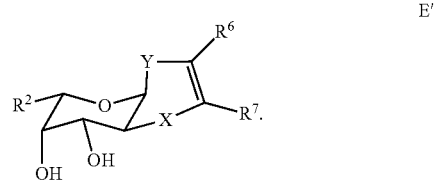

In preferred embodiments, the fucose mimetic of the invention comprises a fucose-like pyranose ring fused to an oxathine ring comprising a phenyl acetic group. The invention further provides methods for the stereoselective synthesis of the fucose mimetics of the invention.

In some specific embodiments, the fucose mimetic compounds of the invention have the following structures:

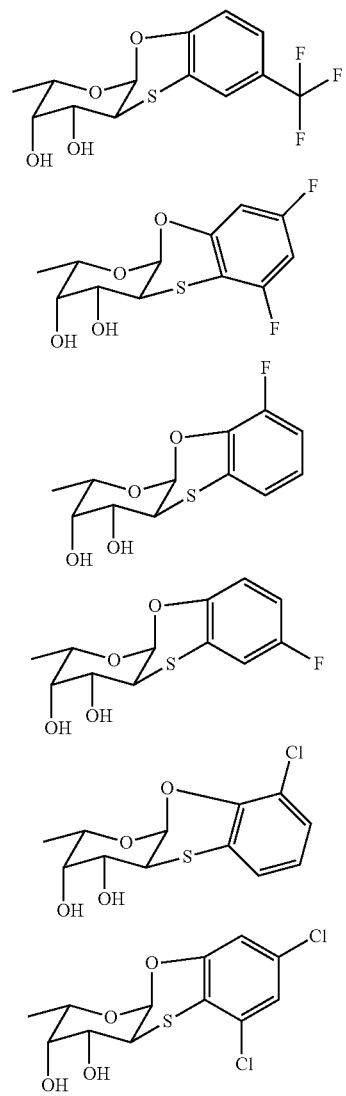

-continued
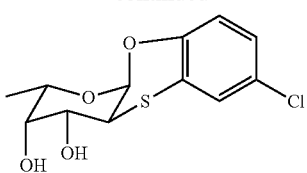
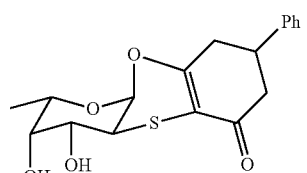
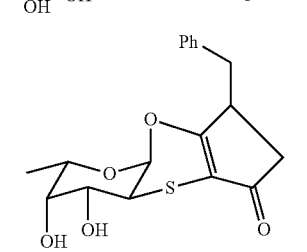
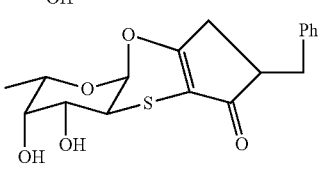
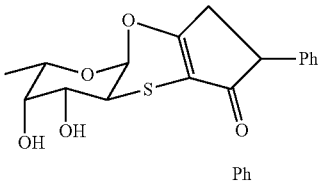
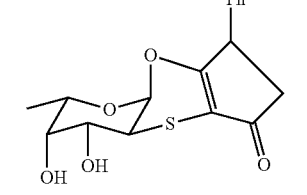
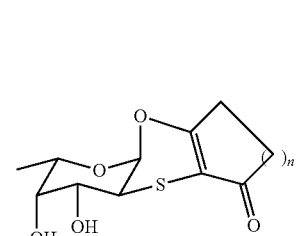
n 0 1-3
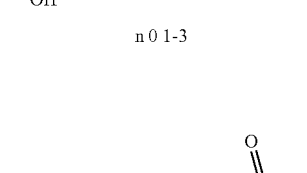
-continued
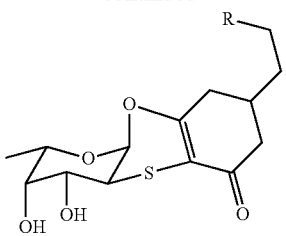
R = alkyl chain
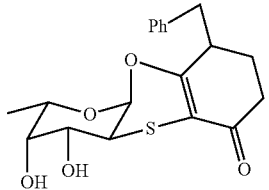
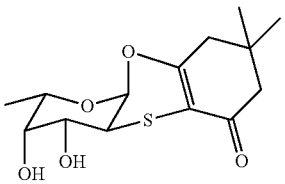
R = alkyl chain
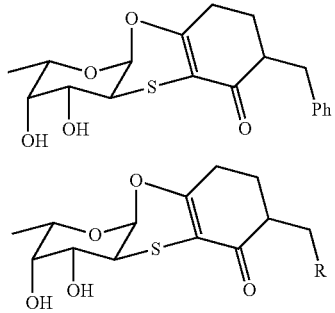
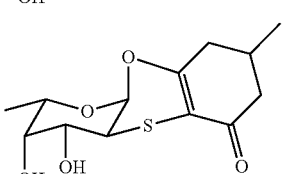
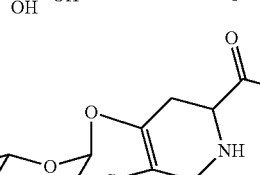
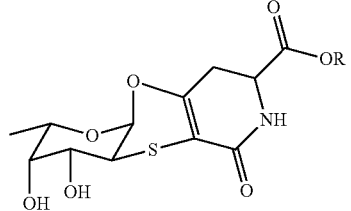
R = H, CH$_3$
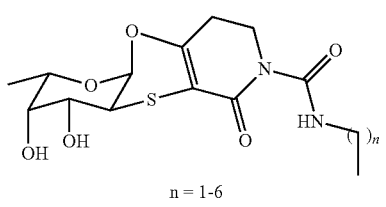
n = 1-6

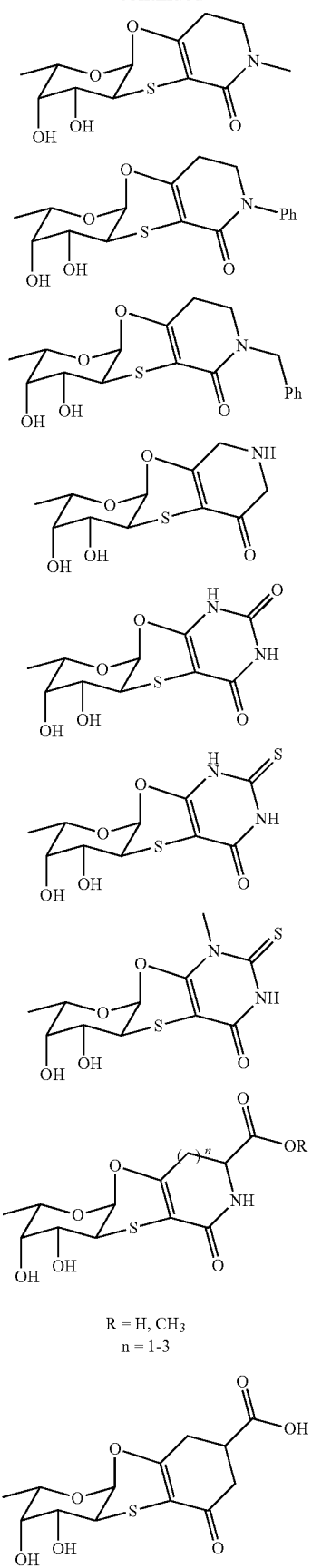
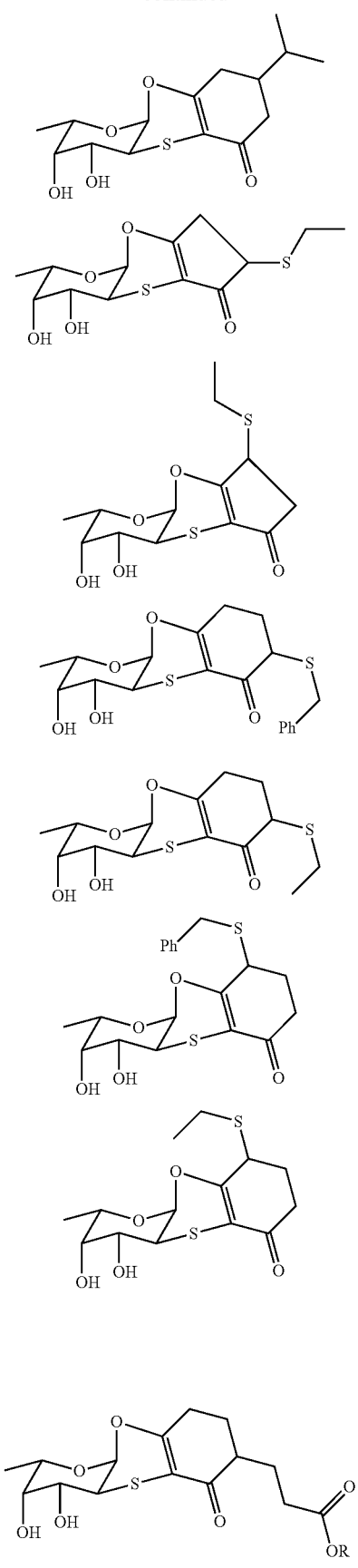
R = H, CH₃
n = 1-3

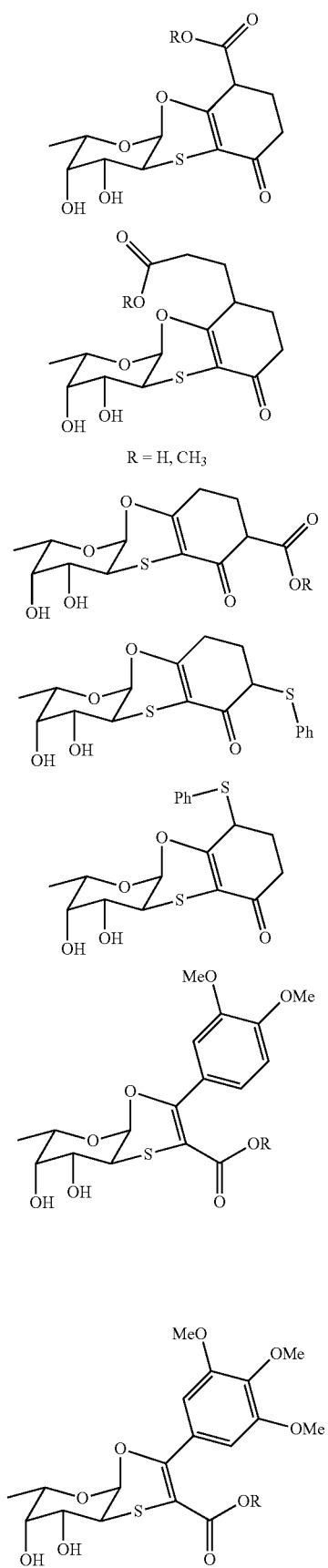
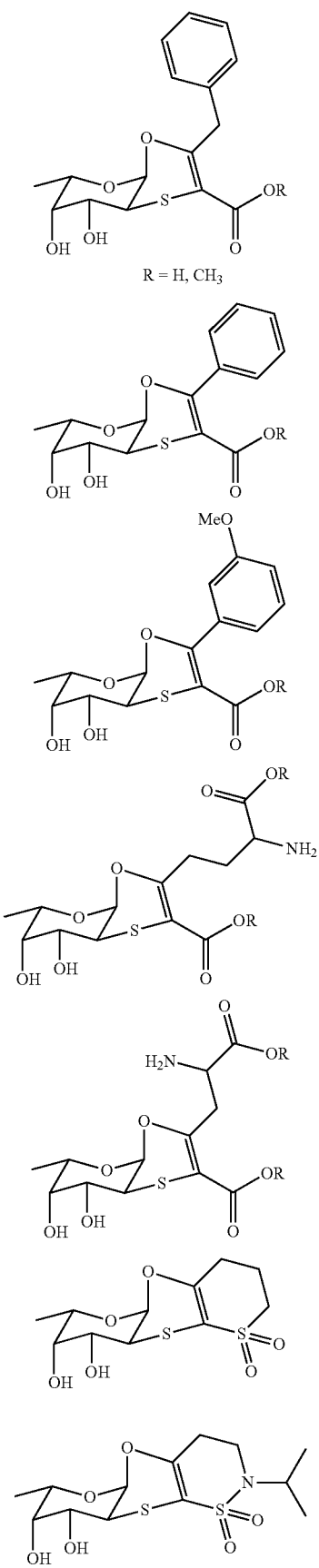

-continued

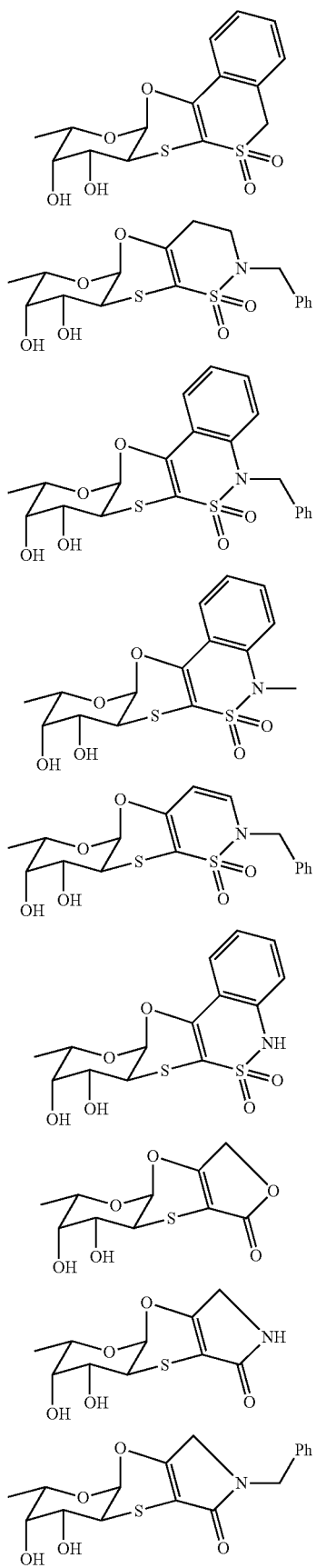

-continued

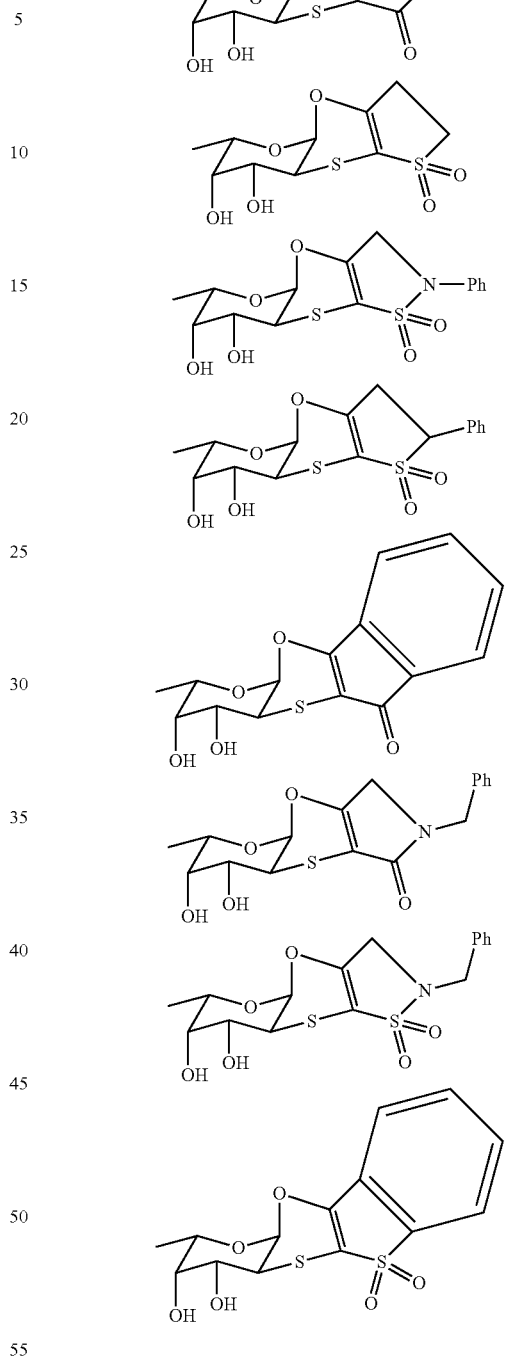

In preferred embodiments, the fucose mimetics are functionalized with Golgi targeting modules to provide a specific targeting of the compounds to the selected organelle.[ref] In particular, Golgi targeting modules can be, but are not limited to, (D/L)-cysteine, mono-, di-, tri-thiols containing modules, fat acids modules with saturated and unsaturated alkyl chains, natural ceramide and related analogues, SNAP-Tag substrate, Halo-Tag substrate, sulphonamide derivatives, or myristoyl-Gly-Cys module.

In some embodiments, the Golgi-targeting modules can be covalently conjugated to the fucose mimetic scaffold. Therefore, $R^1$, $R^2$, $R^3$, $R^4$, $R^5$, $R^6$, $R^7$, R" and/or-R can comprise a Golgi targeting moiety and a cleavable linker. The covalent conjugation can be performed with or without an alkyl/aryl spacer, which spacer can be linked through a bond that is cleavable by a specific stimulus, e.g., pH, enzyme, light, and/or temperature or through a stable bond.

In some embodiments, the compounds of the invention can be included in drug delivery systems as described in 'Pharmaceutical Formulations and Routes of Administration' which can be, but are not limited to, organic and inorganic nanoparticles, nanomaterials, liposomes, micelles, hydrogels, micro- or nano-spheres, mesoporous materials, dendrimers, or dendrons.

Figure 7:
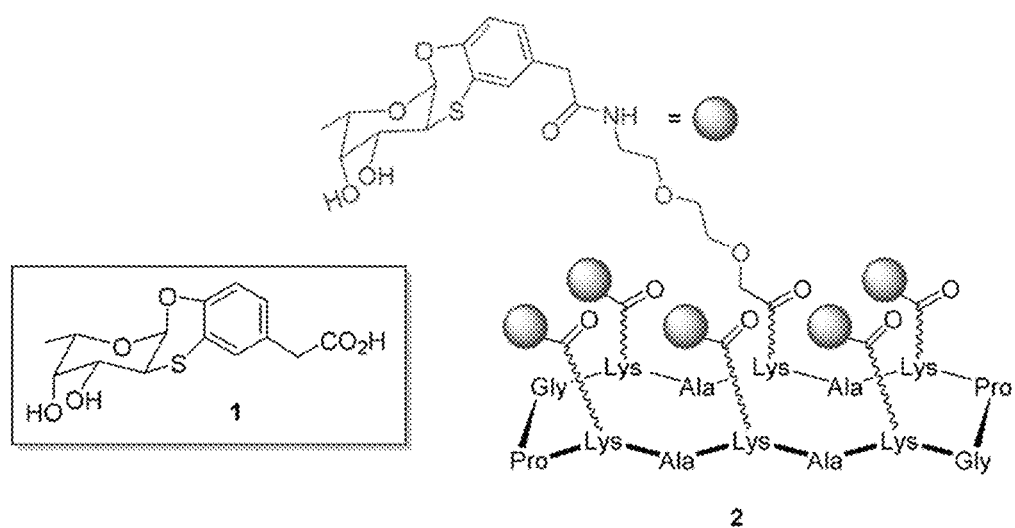
FIG. 7 shows the structure of the fucose mimetic 1 and the hexavalent conjugate 32.

In preferred embodiments, the compounds of the invention interact with fucosyltransferase targets with a mM affinity as described in FIGS. 7A-C and specifically the compounds substantially inhibit the creation of sialyl Lewis X by FTVI and and/or FTVII, but have no significant effect on the creation of Lewis X by FTIX.

In some embodiments, methods for screening compounds for fucosyltransferase inhibitor activity are provided. In some embodiments, the methods comprise exofucosylation techniques whereby a pertinent fucosyltransferase together with GDP-Fucose is placed in a cell suspension to stereoselectively install fucose on pertinent acceptor cell surface glycan(s) in the presence and absence of a compound tested for its fucosyltransferase inhibitor activity. In some embodiments, the methods comprise sheer stress experiments wherein cells treated with a pertinent exofucosyltransferase and GDP-Fucose in the presence and absence of a compound tested for its fucosyltransferase inhibitor activity are loaded in a parallel plate flow chamber seeded with monolayers of cytokine-stimulated human umbilical vein endothelial cells under defined fluid shear conditions to determine an inhibitory effect of the respective compound on the binding of the fucosyltransferase treated cells to the human umbilical vein endothelial cells.

For example, in certain embodiments, the compounds of the invention substantially inhibit a fucosyltransferase VI and/or VII. Such substantial inhibition by the compounds of the invention comprises an inhibition by about, for example, 5% to about 100%, or about 8% to about 90%; about 10% to about 80%, about 15% to about 75%, about 20% to about 70%, about 25% to about 65%, about 30% to about 50%.

In further embodiments, the compounds of the invention do not substantially inhibit fucosyltransferase IX. Such lack of substantial inhibition comprises an inhibition of fucosyltransferase IX by less than 10%, 5%, less than 1% or 0%.

Advantageously, the compounds of the invention provide an effective and selective inhibition of fucosyltransferases and, the methods of the invention using the compounds of the invention provide tailored treatments of glycan-related conditions. Specifically, the compounds of the invention selectively and specifically inhibit target fucosyltransferases so as to provide a custom-modification of cell surface glycans. For example, the compounds of the invention custom-modify cell surface glycans by substantially inhibiting the generation of sialyl Lewis X by FTVI and FTVII with no effect on the generation of Lewis X by FTIX. Thus, the compounds and methods of the invention provide the selective suppression of sialyl Lewis X display on cells of a subject, while leaving Lewis X display on cells of the subject unaffected.

In some embodiments, the pharmaceutical composition is useful for the treatment of a disease associated with one or more of neoplasia (e.g., breast cancer, lung cancer, prostate cancer, lymphoma, leukemia, etc.), immunologic/autoimmune conditions (e.g., graft vs. host disease, multiple sclerosis, diabetes, inflammatory bowel disease, lupus erythematosus, rheumatoid arthritis, psoriasis, etc.), direct tissue injury (e.g., burns, trauma, decubitus ulcers, etc.), ischemic/vascular events (e.g., myocardial infarct, stroke, shock, hemorrhage, coagulopathy, thrombosis, etc.), infections (e.g., cellulitis, pneumonia, meningitis, sepsis, SIRS, respiratory, e.g., coronavirus, COVID-19, SARS, MERS, etc.), degenerative diseases (e.g., osteoporosis, osteoarthritis, Alzheimer's disease, etc.), congenital/genetic diseases (e.g., epidermolysis bullosa, osteogenesis imperfecta, muscular dystrophies, lysosomal storage diseases, Huntington's disease, etc.), adverse drug effects (e.g., drug-induced hepatitis, drug-induced cardiac injury, etc.), toxic injuries (e.g., radiation exposure(s), chemical exposure(s), alcoholic hepatitis, alcoholic pancreatitis, alcoholic cardiomyopathy, cocaine cardiomyopathy, etc.), metabolic derangements (e.g., uremic pericarditis, metabolic acidosis, etc.), iatrogenic conditions (e.g., radiation-induced tissue injury, surgery-related complications, etc.), and/or idiopathic processes (e.g., amyotrophic lateral sclerosis, Parsonnage-Turner Syndrome, etc.). In some embodiments, the pharmaceutical composition is useful for the treatment of a disease associated with a cytokine storm. In some embodiments, the pharmaceutical composition is useful for effecting immunohomeostasis in a subject. In some embodiments, the pharmaceutical composition according to any preceding claim is useful for the treatment of COVID-19. In some embodiments, the subject is a human. Advantageously, the selective suppression of sialyl Lewis X on cells using the methods and compounds of the invention provides treatments of conditions in which sialyl Lewis X is involved in the genesis and/or progression of the condition. For example, sialyl Lewis X is involved in leukocyte trafficking, human fertilization, metastasis, immune cell differentiation, and disease progression in cystic fibrosis. Therefore, the methods of the instant invention provide treatments for subjects that suffer from a variety of conditions, such as colorectal cancer (CRC), or non-small cell lung cancer (NSCLC), in which a reduction in sialyl Lewis X could prevent the initiation and/or progression of metastatic disease, or in the treatment of certain types of chronic inflammation, such as in colitis, or arthritis.

In some embodiments, the methods of the invention comprise treating a subject who suffers from a disease or condition that can be treated and/or prevented by a modification of fucosylated cell surface glycoconjugates, wherein the method comprises administering to the subject a therapeutically effective amount of a fucosyltransferase inhibitor and a pharmaceutical acceptable carrier. In some embodiments, a composition is administered to a subject wherein the composition comprises any of the compounds according to the instant invention.

In some embodiments, the methods of the invention treat a subject who suffers from an acute inflammatory disease, a chronic inflammatory disease, type 1 and type 2 diabetes, cystic fibrosis, or a cancer.

For example, the compounds of the invention can reduce the levels of sialyl Lewis X on cells of cystic fibrosis (CF) patients such that the increased fucosylation and the increased formation of sialyl Lewis X on CF mucins is reduced and recurrent infections in CF patients that remain the underlying cause of most morbidity and mortality in CF patients are reduced.

In some embodiments, the compounds of the invention are administered to a subject suffering from a cancer, wherein the compound of the invention reduces the levels of sialyl Lewis X on cancer cells and, consequently, reduces the interaction of cancer cells with platelets and endothelial cells thereby reducing tumor cell vascular extravasation and reduces tumor cell evasion from anti-tumor immunity by forming a "cloak" of bound platelets.

In some embodiments, the methods of the invention treat a subject who suffers from cancer and the methods of the invention further comprise administering a composition of the invention directly into a tumor, a tissue surrounding the tumor and/or a blood vessel supplying the tumor.

In some embodiments, the compounds of the invention are administered to a subject suffering from a blood cancer, for example, Hodgkin disease, B-cell chronic lymphocytic leukemia, acute lymphoblastic leukemia, or acute non-lymphocytic leukemia.

In some embodiments, the compounds of the invention are administered to a subject suffering from a solid cancer, for example, an adenocarcinoma of the lung, the breast or the colon; a small cell lung cancer; or a non-small cell lung cancer In some embodiments, the methods of the invention treat a subject who suffers from an acute inflammatory disease, for example, a reperfusion injury, a septic shock, a bacterial infection, a viral infection, or a parasitic infection.

For example, the compounds of the invention can be administered to a subject suffering from an infection with *Pseudomonas aeruginosa* or *Helicobacter pylori* or a helminth infection such as *S. mansoni* or *Ascaris suum*.

In some embodiments, the methods of the invention treat a subject who suffers from a chronic inflammatory disease, for example, asthma, chronic obstructive pulmonary disease (COPD), rheumatoid arthritis, or juvenile idiopathic arthritis.

In some embodiments, the methods of the invention comprise administering the composition directly to a site of inflammation in the subject. Advantageously, the fucose mimetic and/or analog compounds of the invention interfere with the catalytic activity of fucosyltransferases and inhibit the addition of GDP-Fucose donor to an acceptor molecule, thereby inhibiting the synthesis of fucosylated glycans.

Because of the highly selective inhibition of fucosyltransferases provided by the compounds of the instant invention, the compounds of the invention can inhibit cell-cell interactions that are based on sialyl Lewis X without inhibiting cell-cell interactions that are based on Lewis X. Consequently, the compounds of the invention have lower levels of side effects when administered to a subject compared to less selective fucosyltransferase inhibitors and the compounds of the invention can be administered in higher amounts to a subject compared to less selective fucosyltransferase inhibitors to treat sialyl Lewis X-related conditions.

In some embodiments, the methods of the invention comprise administering at least one compound of the invention to a cell that naturally expresses sialyl Lewis X and inhibit said natural sialyl Lewis X expression on said cell. For example, a cell treated with a compound of the invention can be, but is not limited to, an endothelial cell, a thrombocyte, a cancer cell, a leukocyte, a hematopoietic stem cell, a B cell, a dendritic cell, a monocyte, a NK cell, and/or a T cell.

In yet further preferred embodiments, the method of the invention comprises administering a fucosyltransferase inhibitor that selectively inhibits a fucosyltransferase selected from a fucosyltransferase VI and fucosyltransferase VII and does not inhibit a fucosyltransferase IX with a compound or composition that is known to treat a condition including, but not limited to, a condition in which leukocyte trafficking, fertilization, metastasis, and immune cell differentiation plays a role for initiation and/or progression of the condition.

In some embodiments, the methods of the invention comprise treating a subject that suffers from a condition that can be treated and/or prevented by a modification of fucosylated cell surface glycoconjugates, wherein the modification of fucosylated cell surface glycoconjugates comprises a reduction of sialyated Lewis X on a cell surface.

In some embodiments, the methods of the invention comprise treating a subject with a compound of the invention that does not reduce or change the expression of Lewis X on a cell.

In some embodiments, the methods of the invention comprise treating a subject with a compound of the invention to reduce the amount of binding interactions between a subject's selectins and sialyl Lewis X and related sialylated, fucosylated glycans.

In some embodiments, the methods comprise administering a compound of the invention to inhibit the binding interactions between a sugar-binding cell adhesion protein including, but not limited to, an E-selectin, a P-selectin and/or a L-selectin and inhibit the binding interactions of cells including, but not limited to leukocytes, thrombocytes, lymphocytes, endothelial cells, and cancer cells.

In further embodiments, the methods comprise administering a compound of the invention to inhibit the binding interaction between a bacterium, a virus, and/or a parasite and a cell of a subject.

In yet further embodiments, the methods of the invention comprise administering a compound of the invention to a cell that is used to generate a vaccine product. Specifically, by treating a cell that produces a compound or molecule that is a vaccine and is administered to a subject, the presence of sialyl Lewis X moieties on the vaccine compound or molecule are reduced, thereby increasing the antigenicity of the compound or molecule.

Definitions

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising".

The transitional term "comprising," which is synonymous with "including," or "containing," is inclusive or open-ended and does not exclude additional, un-recited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the term "comprising" contemplates other embodiments that "consist" or "consist essentially of" the recited component(s).

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the terms "about" or "approximately" are used, these compositions contain the stated amount of the ingredient with a variation (error range) of 0-10% around the value (X±10%).

"Subject" refers to an animal, such as a mammal, for example a human. The methods described herein can be useful in both humans and non-human animals. In some embodiments, the subject is a mammal including an animal of an animal model of a disease and in some embodiments, the subject is human. The terms "subject" and "subject" can be used interchangeably. Mammalian species that can benefit from the disclosed methods and compounds of the instant invention include, but are not limited to, apes, chimpanzees, orangutans, humans monkeys; and domesticated animals such as dogs, cats, horses, cattle, pigs, sheep, goats, chicken, mice, rats, guinea pigs, and hamsters.

"Treatment", "treating", "palliating" and "ameliorating" (and grammatical variants of these terms), as used herein, are used interchangeably. These terms refer to an approach for obtaining beneficial or desired results including but not limited to therapeutic benefit. A therapeutic benefit is achieved with the eradication or amelioration of one or more of the physiological symptoms associated with the underlying disease such that an improvement is observed in the subject, notwithstanding that the subject may still be afflicted with the underlying disease. A treatment includes delaying the appearance of a disease or condition, delaying the onset of symptoms of a disease or condition, slowing, halting, or reversing the progression of a disease or condition, or any combination thereof.

"Administration" or "administering" as used herein refer to the process in which the fucose mimetic compounds of the instant invention are delivered to a subject for treatment. Administering includes, but is not limited to, delivering intravenous, intramuscular, intraperitoneal, intraarterial, intrathecal, subcutaneous, aerosolized, inhaled, oral, topical, transdermal, rectal, vaginal and other routes that allow the fucose mimetic to contact a cell of the subject. In further preferred embodiments, the compounds of the invention are administered directly into a tumor afflicted area including, but no limited to, the tumor tissue itself, the tissue surrounding the tumor and/or the blood vessels, specifically the arteries supplying blood to the tumor. The fucose mimetic compounds of the invention can be administered independently or in combination with other compounds. For example, the compounds and compositions of the instant invention can be administered either simultaneously or before or after the administration of a therapeutic compound or composition that is known to treat a condition including, but not limited to, a condition in which leukocyte trafficking, human fertilization, metastasis, and immune cell differentiation play a role for initiation and/or progression of the condition. Further, the compounds and compositions of the instant invention can be administered either simultaneously or before or after the administration of another therapeutic compound or composition.

The terms "simultaneous" or "simultaneously" as applied to administering therapies to a subject refer to administering one or more therapies at the same time, or at two different time points that are separated by no more than 30 minutes. The term "after or before" as applied to administering therapies to a subject refers to administering more than one doses at two different time points that are separated by more than 30 minutes, e.g., about 1 hour, about 2 hours, about 5 hours, 8 hours, 1 day, 2 days, 3 days, 4 days, 5 days, 6 days, 7 days or even longer.

As used herein, the term "cancer" refers to the presence of cells possessing abnormal growth characteristics, such as uncontrolled proliferation, immortality, metastatic potential, rapid growth and proliferation rate, perturbed oncogenic signaling, and certain characteristic morphological features. This includes, but is not limited to, the growth of: (1) benign or malignant cells with normal levels of lectins (e.g., tumor cells); or (2) benign or malignant cells (e.g., tumor cells) with abnormally high levels of lectins.

In some embodiments, the compounds of the invention are administered directly to a site of inflammation in a subject. A site of inflammation includes, but is not limited to, a joint, a lobe of a lung, a sinus, a reperfused organ, a cerebral ventricle, a spinal cord, a subarachnoidal space, a bladder, a pancreas, a kidney, a bowel, and/or a prostate.

The term "effective amount" or "therapeutically effective amount" refers to that amount of an inhibitor described herein that is sufficient to effect the intended application including but not limited to disease treatment. The therapeutically effective amount may vary depending upon the intended application (in vitro or in vivo), or the subject and disease and/or condition being treated, e.g., the weight and age of the subject, the severity of the disease and/or condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

"Pharmaceutically acceptable carrier" refers to a diluent, adjuvant or excipient with which the one or more active agents disclosed herein can be formulated. Pharmaceutically acceptable carriers or excipients include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the mimetics and compounds of the invention, their use in the compositions of the invention is contemplated. Typically, a "pharmaceutically acceptable carrier" is a substance that is non-toxic, biologically tolerable, and otherwise biologically suitable for administration to a subject, such as an inert substance, added to a pharmacological composition or otherwise used as a diluent, adjuvant or excipient to facilitate administration of the composition disclosed herein and that is compatible therewith.

"Protecting group" refers to a group of atoms that, when attached to a reactive functional group in a molecule, mask, reduce or prevent the reactivity of the functional group. Typically, a protecting group may be selectively removed as desired during the course of a synthesis, or in response to respond to external/internal stimuli (e.g., pH, enzyme, light, oxidation, and/or temperature dependent). Examples of protecting groups can be found in Greene and Wuts, Protective Groups in Organic Chemistry, 3rd Ed., 1999, John Wiley & Sons, NY and Harrison et al., Compendium of Synthetic Organic Methods, Vols. 1-8, 1971-1996, John Wiley & Sons, NY. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPPS groups), glycol ethers, such as ethylene glycol and propylene glycol derivatives and allyl ethers.

Pharmaceutical Formulations and Routes of Administration

Examples of carriers suitable for use in the pharmaceutical compositions are known in the art and such embodiments are within the purview of the invention. The pharmaceutically acceptable carriers and excipients, including, but not limited to, aqueous vehicles, water-miscible vehicles, non-aqueous vehicles, stabilizers, solubility enhancers, isotonic agents, buffering agents, suspending and dispersing agents, wetting or emulsifying agents, complexing agents, sequestering or chelating agents, cryoprotectants, lyoprotectants, thickening agents, pH adjusting agents, and inert gases. Other suitable excipients or carriers include, but are not limited to, dextran, glucose, maltose, sorbitol, xylitol, fructose, sucrose, and trehalose. In addition, drug delivery systems including, but are not limited to organic and inorganic micro- or nanoparticles, nanomaterials, liposomes, micelles, hydrogels, micro- or nano-spheres, mesoporous materials, dendrimers, dendrons.

Preferably, micro- or nanoparticles are made of substantially biologically inert or biologically compatible materials. The terms "inert," "biologically inert" or "biologically compatible," as used herein, refer to substances or materials that, after the normal healing period when administered into living tissues, do not elicit substantially adverse biochemical, allergic, or unwanted immune responses. Preferably, the micro- or nanoparticles of the invention are biodegradable. The term "biodegradable," as used herein, refers to the ability of materials to be broken down by normal chemical, biochemical and/or physical processes including erosion, dissolution, corrosion, degradation, hydrolysis, and abrasion and combinations thereof Biocompatible materials useful for making the micro- or nanoparticles of the invention include, but are not limited to, bio-degradable polymeric materials including, but not limited to, hydrogels, collagen, alginate, poly(glycolide) (PGA), poly(L-lactide) (PLA), poly(lactide-co-glycolide) (PLGA), polyethylene glycol (PEG), polyesters, polyanhydrides, polyorthoesters, polyamides; non-polymeric biodegradable ceramic materials including, but not limited to, calcium phosphate, hydroxyapatite, tricalcium phosphate, and combinations thereof In preferred embodiments, the micro- or nanoparticles of the invention are fabricated from poly(lactic-co-glycolic acid) (PLGA), which is FDA approved for delivery of therapeutics.

In some embodiments, the compositions of the invention comprise a therapeutically effective amount of a micro- or nanoparticle according to the instant invention and, optionally, a pharmaceutically acceptable carrier. The micro- or nanoparticles and therapeutic compositions of the invention may be delivered to tissues or organs of a subject in need of a treatment with such micro- or nanoparticles and therapeutic compositions. The compositions of the invention comprising micro- or nanoparticles can be administered in a single dose or in more than one dose over a period of time to confer the desired effect. In some embodiments, the micro- or nanoparticles of the invention are formulated for parenteral administration. In some embodiments, the micro- or nanoparticles comprising the compositions of the invention are formulated as a sustained-release formulation. In some embodiments, the micro- or nanoparticles of the invention are administered in combination with other pharmacological therapies. Combination therapies with other medicaments targeting similar or distinct disease mechanisms have advantages of greater efficacy and safety relative to respective monotherapies. The micro- or nanoparticles of the invention when administered in combination with other pharmacological therapies can be administered simultaneously or sequentially in time. The fucose mimetic compounds of the instant invention can be administered as a pharmaceutically acceptable salt. The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In some embodiments, the compositions of the invention are aqueous solutions containing one or more fucose mimetic compounds of the invention in admixture with excipients suitable for the manufacture of aqueous solution. Such excipients include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending one or more fucose mimetic compounds in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. Sweetening agents can be added to provide a palatable oral preparation. These formulations can be preserved by the addition of an antioxidant such as ascorbic acid.

The pharmaceutical formulations of the subject invention can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening and flavoring agents. Syrups and elixirs can be formulated with sweetening agents, such as glycerol, sorbitol or sucrose. Such formulations can also contain a demulcent, a preservative, a flavoring or a coloring agent.

Compositions comprising a compound of the invention together with a conventional adjuvant, carrier, or diluent, may thus be placed into the form of solids including tablets, filled capsules, powder and pellet forms, and liquids such as aqueous or non-aqueous solutions, suspensions, emulsions, elixirs, and capsules filled with the same. The composition may further comprise conventional ingredients in conventional proportions, with or without additional active compounds.

In further embodiments, the compositions of the invention are in the powder form. For example, the pharmaceutically accepted carrier is a finely divided solid, which is in a mixture with the finely divided active compounds. In other embodiments, the composition is in the tablet form. The active components are mixed with the pharmaceutically accepted carrier having the necessary binding capacity in suitable proportions and compacted in desired shape and size. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

In some embodiments, the compositions are in other solid forms including, but not limited to, capsules, pills, cachets, and lozenges, which are suitable for oral administration.

In further embodiments, the compositions are in other solid forms including capsules, pills, cachets, and lozenges, which are suitable for oral administration.

In some embodiments, the compositions are formulated in accordance with routine procedures as pharmaceutical compositions adapted for local administration to humans. Typically, compositions for local administration are solutions in a sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active compound. Where the composition is administered by injection, an ampoule of sterile water for injection or saline can be provided so that the ingredients may be mixed prior to administration.

The pharmaceutical compositions may be formulated in any forms that are suitable for parenteral administration, including solutions, suspensions, emulsions, micelles, liposomes, microspheres, nanosystems, semi-solid, and solid forms suitable for solutions or suspensions in liquid prior to injection.

For the specific fucose mimetic compounds of the invention, the therapeutically effective concentration can be between about 1 pM to about 1 M. In some embodiments the range of fucose mimetic concentration is between about 100 pM to about 500 mM. In some embodiments, the therapeutically effective concentration of the fucose mimetic is about 1 µM to about 500 mM.

The amount of fucose mimetic compound administered can be an amount from a low of about 1 pM, about 200 pM, about 500 pM, about 1 nM, about 500 nM; about 1 µM, about 10 µM; about 50 µM, or about 100 µM to a high of about 1 M; about 750 mM; about 500 mM; about 100 mM to about 1 mM. For example, the amount of fucose mimetic of the subject invention can be from about 10 pM to about 900 mM; from about 100 pM to about 800 mM; about 200 pM to about 500 mM; about 500 pM to about 200 mM; about 800 pM to about 100 mM; about 1 µM to about 80 mM; about 10 µM to about 50 mM; about 50 µM to about 20 mM; about 80 µM to about 10 mM; about 100 µM to about 1 mM; about 150 µM to about 800 µM; about 180 µM to about 600 µM; about 200 µM to about 400 µM; and about 250 µM to about 350 µM.

The fucose mimetics of the invention can be administered in a therapeutic amount or a sub-therapeutic amount. A "sub-therapeutic amount" of a fucose mimetic is an amount less than the effective amount for that fucose mimetic, but which when combined with an effective or sub-therapeutic amount of another therapeutic compound or therapy can produce a desired result, due to, for example, synergy in the resulting efficacious effects (e.g., therapeutic benefit) for the subject, or reduced side effects associated with the compounds administered to the subject. Typical therapeutic amounts for an agent, as disclosed herein, can be ascertained by a skilled clinical scientist depending on the subject to be treated and the disease and/or condition to be treated. Subtherapeutic amounts of a fucose mimetic, as provided herein, are amounts less than those used as typical therapeutic amounts.

Depending on the route of administration, the pharmaceutical composition can be associated with a material to protect the pharmaceutical composition from the action of enzymes, acids, and other natural conditions that may inactivate the pharmaceutical composition. Dispersions can also be prepared in glycerol, liquid polyethylene glycols, and mixtures thereof, and in oils. Under ordinary conditions of storage and use, these preparations may contain a preservative to prevent the growth of microorganisms.

In specific embodiments, the composition of the subject invention may be administered at least once a day, twice a day, or three times a day for consecutive days, e.g. 2, 3, 4, 5, 6, 7, 8, 9, 10, 11, 12, 13, 14, 15, 16, 17, 18, 19, 20, 21, 22, 23, 24, 25, 26, 27, 28, 29, or 30 days. The composition of the subject invention may also be administered for weeks, months or years.

Conditions to be Treated

In some embodiments, a method for treating a subject is provided, the method comprising administering a therapeutically effective amount of a fucosyltransferase inhibitor and a pharmaceutical acceptable carrier. In some embodiments, the methods of the invention comprise administering more than one fucosyltransferase inhibitor that is selective for a fucosyltransferase that generates sialyl Lewis X. In further preferred embodiments, the method of the invention comprises administering at least one fucosyltransferase inhibitor with a compound or composition that is known to treat a condition including, but not limited to, a condition in which leukocyte trafficking, fertilization, metastasis, and immune cell differentiation play a role for initiation and/or progression of the condition.

In preferred embodiments, the methods of the invention comprise treating a condition including, but not limited to, an acute inflammatory disease, a chronic inflammatory disease, or a cancer. The acute inflammatory disease treated using the compounds of the invention can be, for example, a reperfusion injury, septic shock, a bacterial infection, a viral infection, and/or a parasitic infection.

The chronic inflammatory disease treated using the compounds of the invention can be, for example, asthma, chronic obstructive pulmonary disease (COPD), cancer, diabetes, rheumatoid arthritis, juvenile idiopathic arthritis, or cystic fibrosis.

In some embodiments, the methods and compounds of the invention are used to prevent fertilization in a subject, for example, by administering a composition according to the invention as contraceptive.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

MATERIAL AND METHODS

Exofucosylation of the RPMI-8402 Cells Line Using FTVI and GDP-Fuc

A titration of GDP-Fucose was carried out to determine the maximum mean fluoresent intensity (MFI) of sLe$^X$ and Le$^X$ via flow cytometry for downstream inhibition experiments. Generally, $1 \times 10^6$ cells were used in each FTVI exofucosylation reaction and all reactions were carried out in triplicate. Cells were then stained with either Alexa-Fluor 488 Mouse Anti-Human CD15s (BD Biosciences), or APC anti-human CD15 (SSEA-1) Antibody (BioLegend). Cells were then acquired on a Canto II (BD Biosciences) flow cytometer and analylized using Flowjo software (Treestar). FTVI was purchased from R&D systems.

Antibodies, Flow Cytometric Analysis

A Canto II (BD Biosciences) flow cytometer was utilized for flow cytometry and the data acquired was analyzed using FlowJo Software (Treestar). Cells were stained using antibodies specific to sLe$^X$ (Alexa-Fluor 488 Mouse Anti-Human CD15s (BD Biosciences)), or Le$^X$ (APC anti-human CD15 (SSEA-1) Antibody (BioLegend)).

Inhibition of Exofucosylation of the RPMI-8402 and MSC Cells Using Fucose Mimetic 1

Cells of the RPMI-8402 cell line and MSC cell line were treated with either 0.3 ug of fucosyltransferase VI (FTVI), 2.7 ug of fucosyltransferase VII (FTVII), 1.0 ug fucosyltransferase IX (FTIX) or buffer-only at 37° C. for 60 minutes. All reactions contained at $1 \times 10^6$ cells/30 ul in HBSS with 10 mM Hepes, 0.1% Human Serum Albumin, and 1.0 mM GDP fucose (GDP-Fuc) (Carbosynth) and the appropriate fucosytransferase. Then, mimetic 1 was added to each of the treatment groups in molar equivalents with respect to GDP-Fuc with each of the fucosytransferases. The treatment groups were as follows: 1:1 GDP-Fuc to mimetic 1 (i.e., 1.0 mM GDP-Fuc and 1.0 mM mimetic), 1:2 GDP-Fuc to mimetic 1 (i.e., 1.0 mM GDP-Fuc and 2.0 mM mimetic), or preincubated in presence of FT with a 2.0 mM solution of the mimetic 1 for 45 minutes followed by addition of a 1.0 mM solution of GDP-Fuc for 1 hour. Concentrations of the various FTs were utilized that would maximize the MFI to allow the detection of the efficacy of mimetic 1 to inhibit the various enzymes.

Parallel Plate Flow Chamber

Human umbilical vein endothelial cells (HUVEC, Lonza) were cultured in Endothelial Cell Growth Media (R&D Systems) in Bioflux microfluidic chambers that had been previously coated with 250 ug/ml fibronectin (BD Biosciences). Then 4 hours prior to rolling assay, cells were activated with 40 ng/ml TNFα (R&D Systems). Different cell subsets, based on exofucoslylation/mimetic conditions, were then infused into the chamber at a concentration of $2 \times 10^6$/ml and shear stress was applied from 0.5-8 dynes/cm$^2$. Then RPMI-8402 subsets were loaded into chambers containing monolayers of E-selectin bearing HUVECs with an initial shear rate of 0.5 dyne/cm$^2$, with stepwise increments in the shear rate up to 8 dynes/cm$^2$. The number of tethering/interacting RPMI-8402 cells on HUVEC were quantified at each shear rate and averaged across three different fields of view.

It should be understood that the examples and embodiments described herein are for illustrative purposes only and that various modifications or changes in light thereof will be suggested to persons skilled in the art and are to be included within the spirit and purview of this application.

EXAMPLE 1

Synthesis of Mimentic 1

The synthesis of the fucose mimetic 1 relied on a totally diastereoselective inverse electron demand [4+2] Diels-Alder reaction between an O-thioquinone 2 and a protected L-fucal 3 according to Scheme 1 below:

Scheme 1 Synthesis of the fucose mimetic 1.

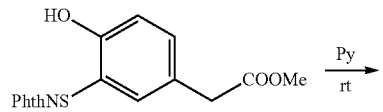

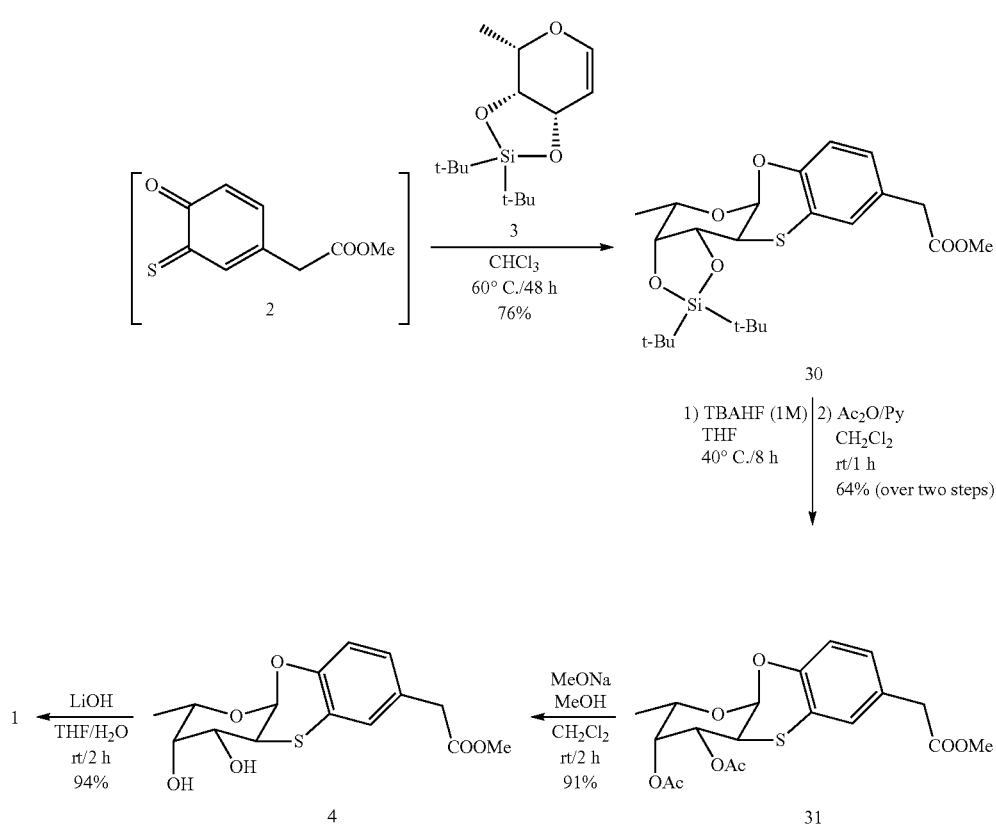

According to Richichi et al., Org. Biomol. Chem., 2013, 11, 4086, which is incorporated in its entirety herewith, to a stirred solution of 4 (0.051 g, 0.156 mmol) in THF (7.0 mL), 607 μL of a 1 M solution of LiOH in $H_2O$ were added. The mixture was stirred for 2 h at rt and then a 1 M solution of $H_3PO_4$ was added to reach pH 6.0. Evaporation of the solvent under vacuum gave a crude which was suspended in a mixture of AcOEt-MeOH 1:4 and filtered. Evaporation of the solvent gave 1 (45 mg, 94%) as white solid, $[\alpha]^{25}$ −93.54 (c 0.31 in $CH_3OH$); mp: 188-191° C.; $^1$H NMR (400 MHz, $CD_3OD$): δ 6.92-6.91 (A part of an ABC system, $J_{AB}$=2.4 Hz, 1H, H-a), 6.85-6.82 (B part of an ABC system, $J_{BC}$=8.0 Hz, $J_{BA}$=2.0 Hz, 1H, H-b), 6.68-6.66 (C part of an ABC system, $J_{CB}$=8.4 Hz, 1H, H-c), 5.49 (d, $J_{1,2}$=2.8 Hz, 1H, H-1), 4.12 (aq, J=6.4 Hz, 1H, H-5), 3.59 (A part of an ABC system, $J_{AB}$=3.2 Hz, $J_{4,5}$=1.2 Hz, 1H, H-4), 3.54 (B part of an ABC system, $J_{BC}$=10.8 Hz, $J_{BA}$=3.2 Hz, 1H, H-3), 3.36 (s, 2H, $CH_2CO_2CH_3$), 3.30 (C part of an ABC system, $J_{CB}$=11.2 Hz, $J_{2,1}$=3.2 Hz, 1H, H-2), 1.17 (d, $J_{6,5}$=6.4 Hz, 3H, H-6); $^{13}$C NMR (100 MHz, $CD_3OD$): δ 175.5(Cq), 152.5 (Cq), 129.7 (C-a), 128.8 (Cq), 128.2 (C-b), 118.7 (C-c), 115.9 (Cq), 96.9 (C-1), 73.0 (C-5), 70.0 (C-4), 68.6 (C-3), 41.2 (C-2), 40.9 ($CH_2COOH$), 16.8 (C-6); HRMS m/z: calcd for C14H16O6NaS [M+Na]+335.05598, found 335.05606.

EXAMPLE 2

Synthesis of Fucose Mimetics Related to the General Structure C

Fucose mimetics 5 and 6 are structurally related to compound 1. As disclosed in Scheme 2, mimetic 5 was prepared by direct coupling of the carboxylic group of mimetic 1 with the O-phosphorylethanolamine. Then, mimetic 6 was prepared by the coupling with the activated carboxylic group of mimetic 7 and the N-Boc protected 2-[2-(2-aminoethoxy)ethoxy]ethanamine.

Scheme 2 Synthesis of mimetics 5 and 6.

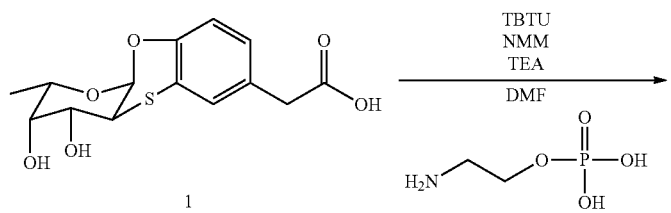

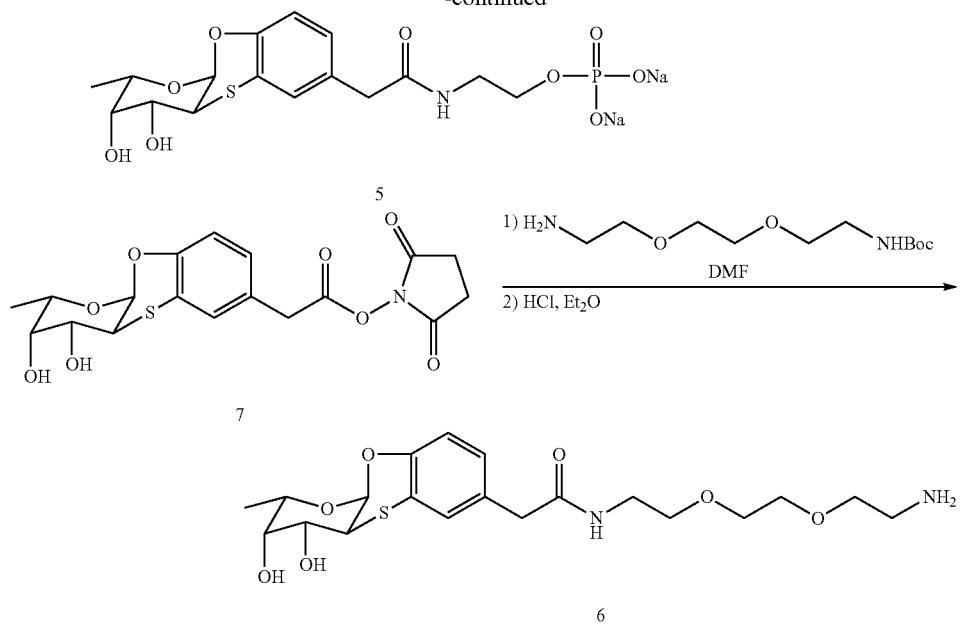

EXAMPLE 3

Synthesis of Fucose Mimetic 5

Structure of Mimetic 5.

To a solution of O-phosphorylethanolamine (37 mg, 0.263 mmol) in DMF (500 µL), TEA (73 µL, 0.525 mmol) was added; the reaction mixture was stirred at r.t. for 20 min. To a solution of 1 (41 mg, 0.131 mmol) in dry DMF (500 µL), TBTU (76 mg, 0.236 mmol) and NMM (26 µL, 0.236 mmol) were added at 0° C.; the reaction mixture was stirred at 0° C. for 5 min and at r.t. for other 5 min. After this, to the reaction mixture of O-phosphorylethanolamine, a solution of 1 was added; the reaction mixture was stirred at r.t. for 24 h. Then, the reaction mixture was concentrated under vacuum to reduce the volume of DMF, diluted with AcOEt (150 mL) and extracted with $H_2O$ (15 mL). The aqueous phase was purified with silica C18 ($H_2O$:MeOH 9:1→$H_2O$:MeOH 7:1→$H_2O$:MeOH 5:1→$H_2O$:MeOH 3:1→$H_2O$:MeOH 1:1), then was filtered with Amberlite IR120 $Na^+$ to give 5 (13 mg, 0.031 mmol) as a white glassy-solid. $[α]_{25}$: +126° ($CHCl_3$, c=0.53); ESI-MS: $[C_{16}H_{21}NO_9PS]^-$ theorical: 434.07, experimental: 434.15; $[C_{32}H_{43}N_2O_{18}P_2S_2]^-$ theorical: 870,1506, experimental: 868.90; $^1$H-NMR (400 MHz, $CDCl_3$) δ: 7.05 (d, $J_{A-B}$=1.8 Hz, 1H, $H_A$), 6.98 (dd, $J_{B-C}$=8.4 Hz, $J_{B-A}$=1.9 Hz, 1H, $H_B$), 6.77 (d, $J_{C-B}$=8.4 Hz, 1H, $H_C$), 5.59 (d, $J_{1-2}$=2.9 Hz, 1H, H-1), 4.22 (aq, J=6.5 Hz, 1H, H-5), 3.91-3.85 (m, 2H, $H_Y$), 3.70 (ad, J=3.0 Hz, 1H, H-3), 3.64 (dd, J=11.0 Hz, J=3.0 Hz, 1H, H-3), 3.41-3.38 (m, 2H, $H_X$), 3.37-3.35 (m, 1H, H-2), 3.30 (s, 2H, $CH_2$), 1.27 (d, $J_{6-5}$=6.5 Hz, 3H, H-6). $^{13}$C-NMR (100 MHz, $CDCl_3$) δ: 127.11 ($C_A$), 126.68 ($C_B$), 117.14 ($C_C$), 95.74 (C1), 71.58 (C4), 68.61 (C5), 67.15 (C3), 62.54 ($C_Y$), 47.97 ($CH_2$), 41.43 ($C_X$), 39.84 (C2), 15.68 (C6).

EXAMPLE 4

Synthesis of Fucose Mimetic 6

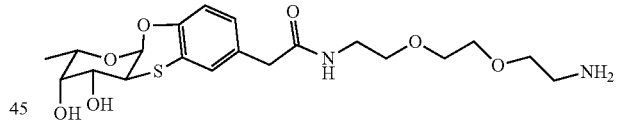

Structure of Mimetic 6.

To a stirred solution of 7 (16 mg, 0.04 mmol) in dry DMF (2.0 mL) the N-Boc protected 2-[2-(2-aminoethoxy)ethoxy]ethanamine was added. The reaction mixture was left to stir at rt overnight, then it was concentrated to dryness. The crude was purified by flash chromatography on silica gel (AcOEt:EP 10:1) to afford 19 mg of compound 21 (95% yield).

Structure of Compound 21:

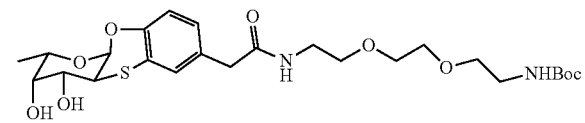

To a stirred solution of 21 (19 mg, 0.035 mmol) in dry DCM (1.0 mL), 90 uL of a 2 M solution of HCl in $Et_2O$ were added. The mixture was stirred for 24 h at rt then toluene was added and the mixture was concentrated to dryness to afford 15 mg of 6 (98% yield).

EXAMPLE 5

Synthesis of Fucose Mimetics Related to the General Structures D and E

Fucose mimetic 8-11 have been prepared by means of a totally diastereoselective cycloaddition between the selected heterodienes and the protected L-fucal 3, as previously reported for analogue glycan derivatives. In particular, mimetic 8 has a structure which is related to the general structure D. The synthetic strategy is disclosed in Scheme 3 and it relies on the hetero Diels Alder reaction between the in situ prepared heterodiene 12 and the protected L-fucal 13. Then, the cycloadduct 14 was in turn deprotected to obtain the fucose mimetic 8.

EXAMPLE 6

Synthesis of Fucose Mimetic 8

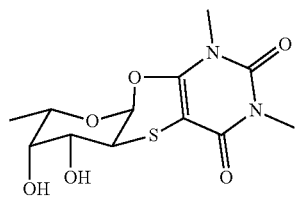

Structure of Fucose Mimetic 8.

Scheme 3. Synthesis of fucose mimetic 8

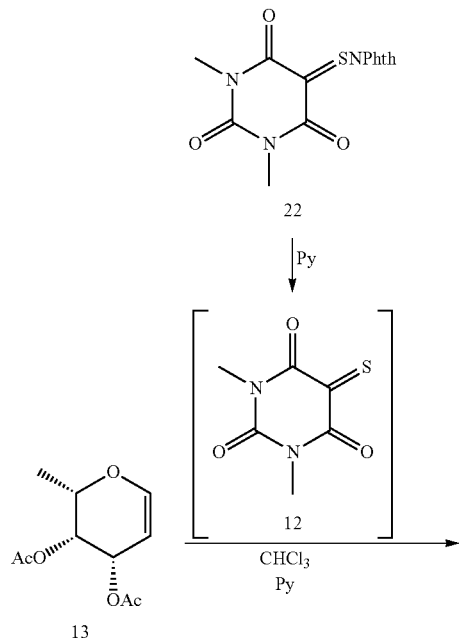

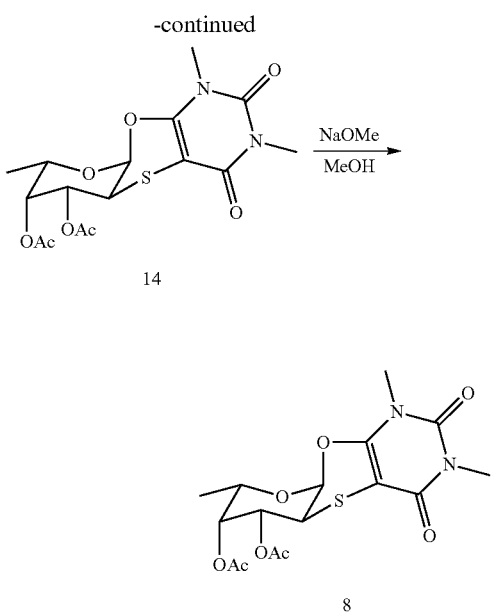

To a stirred solution of 13 (52 mg, 0.24 mmol) in CHCl$_3$ (3.0 mL), 22 (194 mg, 0.58 mmol) and pyridine (195 uL, 190 mg, 2.4 mmol) were added. The reaction mixture was warmed at 45° C. for 96 h, then it was cooled to rt and concentrated to dryness. The crude was purified by flash chromatography on silica gel (AcOEt:EP 1:2) to afford 23 mg of 14 (24% yield). To a stirred solution of 14 (10 mg, 0.025 mmol) in MeOH (500 uL), NaOMe (25 uL of a 1M solution in MeOH) was added. The reaction mixture was stirred for 1 h at rt then the pH was adjusted to 7 with a 1 M solution of HCl in MeOH and the mixture was concentrated to dryness to afford 8.0 mg of compound 8 (>98% yield). $^1$H-NMR (400 MHz, CD$_3$OD) δ: 4.07 (d, 1H, J=8.0 HZ, H-1), 3.64 (ad, 1H, J=3.2 Hz, H-4), 3.44-3.40 (m, 1H, H-5), 3.30 (t, 1H, J=3.6 Hz, 1H, H3), 3.26 (s, 6H, CH$_3$), 2.25 (dd, 1H, J=10.8 Hz, J=8.8 Hz, H-2), 1.20 (d, 3H, J=6.4 Hz, H-6).

EXAMPLE 7

Synthesis of Fucose Mimetic 9

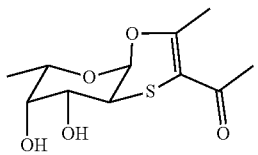

Structure of Fucose Mimetic 9.

Fucose mimetic 9 has a structure which is related to the general structure E. The synthetic strategy is disclosed in Scheme 4 and it relies on the hetero Diels Alder reaction between the in situ prepared heterodiene 15 and the protected L-fucal 3. Then, the cycloadduct 16 was in turn deprotected to obtain the fucose mimetic 9.

Scheme 4. Synthesis of fucose mimetic 9.

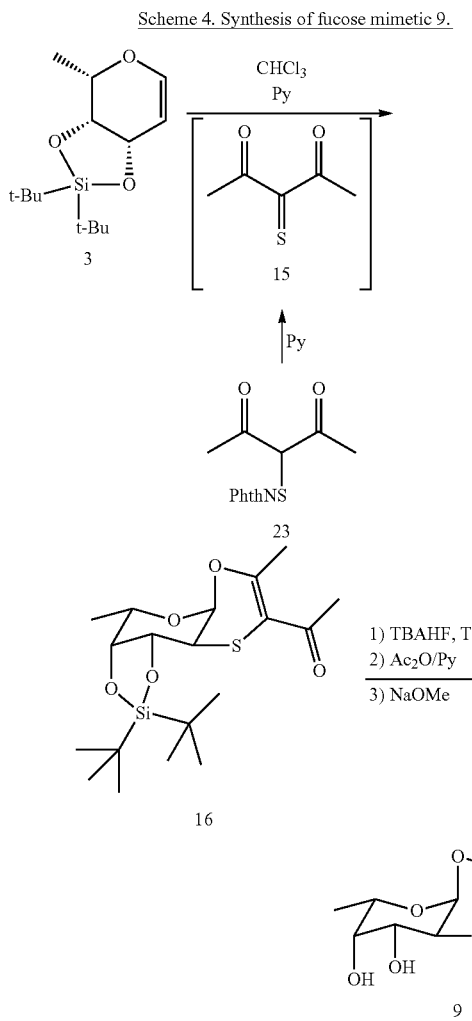

To a solution of 3 (58 mg, 0.2146 mmol) in CHCl$_3$ (1 mL), pyridine (200 μL, 2.14 mmol) and 23 (47.6 mg, 0.171 mmol) were added. The mixture was warmed at 60° C. and stirred for 4 h. After this, pyridine (50 μL, 0.5 mmol) and 23 (12 mg, 0.043 mmol) was added and the reaction mixture was stirred at 45° C. for 9 h. After this, pyridine (100 μL, 1.07 mmol) and 23 (24 mg, 0.086 mmol) was added and the mixture was stirred at 55° C. for 20 h. After this, the reaction mixture was diluted with CHCl$_3$ and the evaporation under vacuum gave a crude, which was purified by flash column chromatography on silica gel (AcOEt:petroleum ether 1:4+ 0.1% triethylamine) to give 16 (55 mg, 64%) as a white solid. [α]$D^{25}$: +102° (CHCl$_3$, c=0.41); ESI-MS: [C19H32NaO5SSi]$^+$ theorical: 423.16, experimental: 423.20; $^1$H-NMR (400 MHz, CDCl$_3$) δ: 5.63 (d, J$_{1-2}$=3.0 Hz, 1H H-1), 4.29 (s, 1H, H-5), 4.13 (at, J=6.4 Hz, 1H, H-4), 3.69-3.66 (m, 1H, H-3), 3.49 (dd, J$_{2-1}$=3.0 Hz, J$_{2-3}$=10.9 Hz, 1H, H-2), 2.34 (s, 3H, CH$_3$), 2.30 (s, 3H, CH$_3$), 1.37 (d, J$_{5-6}$=3.0 Hz, 2H, H-6).

To a stirred solution of 16 (55 mg, 0.14 mmol) a freshly prepared solution of TBAHF (1.2 mL) was added. The reaction mixture was stirred for 2 h at rt then, it was concentrated to dryness. This crude was dissolved in DCM (2.0 mL) and acetic anhydride (103 μL, 1.09 mmol) and pyridine (88 μL, 1.09 mmol) were added. The mixture was stirred at rt for 1 h then, it was diluted with DCM and washed with a saturated solution of NH$_4$Cl (2×20 mL) and with BRINE (2×20 mL). The organic phase was dried over Na$_2$SO$_4$, filtered and concentrated to dryness. The crude was purified by flash chromatography on silica gel (CH$_2$Cl$_2$→CH$_2$Cl$_2$:acetone 20:1) to afford 40 mg of the protected intermediate 24. [α]$^D{}_{25}$: +114° (CHCl$_3$, c=0.37); ESI-MS: [C$_{15}$H$_{20}$NaO$_7$S]$^+$ theorical: 367.08, experimental: 367.12; $^1$H-NMR (400 MHz, CDCl$_3$) δ: 5.67 (d, J$_{1-2}$=3.1 Hz, 1H, H-1), 5.24 (d, J$_{4-3}$=3.1 Hz, 1H, H-4), 5.04 (dd, J$_{3-4}$=3.1 Hz, J$_{3-2}$=11.5 Hz, 1H, H-3), 4.30 (q, J$_{5-6}$=6.5 Hz, 1H, H-5), 3.48 (dd, J$_{2-1}$=3.1 Hz, J$_{2-3}$=11.5 Hz, 1H, H-2), 2.31 (s, 3H, CH$_3$), 2.26 (s, 3H, CH$_3$), 2.19 (s, 3H, CH$_3$), 2.06 (s, 3H, CH$_3$), 1.20 (d, J$_{6-5}$=6.5 Hz, 3H, H-6); $^{13}$C-NMR (100 MHz, CDCl$_3$) δ: 195.45, 160.01, 101.60, 95.84 (C1), 70.18 (C4), 67.04 (C5), 65.86 (C3), 35.60 (C2), 30.25, 21.60, 20.62, 20.58 (CH$_3$), 16.10 (C6).

Structure of the Intermediate 24:

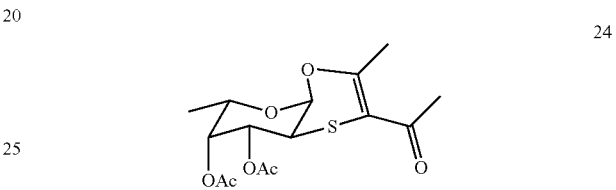

To a solution of 24 (36 mg, 0.104 mmol) in MeOH, K$_2$CO$_3$ anhydrous (4.3 mg, 0.031 mmol) was added (see Scheme 4); the reaction mixture was stirred at rt for 4 h and then concentrated under vacuum. The crude was dissolved in AcOEt and filtered with HPLC filter to remove K$_2$CO$_3$. The crude was filtered on silica gel (AcOEt: petroleum ether 1:1→AcOEt) to give 9 (17 mg, 62%) as a glassy solid. [α]$^D{}_{25}$: +109° (CHCl$_3$, c=0.48); ESI-MS: [C$_{11}$H$_{16}$NaO$_5$S]$^+$ theorical: 283.06, experimental: 283.15; $^1$H-NMR (400 MHz, CDCl$_3$) δ: 5.61 (d, J$_{1-2}$=3.1 Hz, 1H, H-1), 4.14 (q, J$_{5-4}$=6.6 Hz, 1H, H-5), 3-85-3.83 (m, 1H, H-4), 3.66 (dd, J$_{3-2}$=10.6 Hz, J$_{3-4}$=2.5 Hz, 1H, H-3), 3.40 (cd, J$_{2-3}$=10.7 Hz, J$_{2-1}$=3.1 Hz, 1H, H-2), 2.33 (s, 3H, CH$_3$), 2.29 (s, 3H, CH$_3$), 1.36 (d, J$_{6-5}$=6.6 Hz, 3H, H-6); $^{13}$C-NMR (100 MHz, CDCl$_3$) δ: 195.30, 170.28, 158.80, 96.05 (C1), 70.60 (C4), 68.54 (C5), 66.25 (C3), 38.69(C2), 30.16, 21.76 (CH$_3$), 16.35 (C6).

EXAMPLE 8

Synthesis of Fucose Mimetic 10

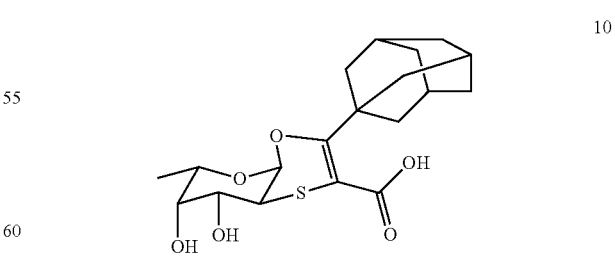

Structure of Fucose Mimetic 10.

Fucose mimetic 10 has a structure which is related to the general structure E. The synthetic strategy is disclosed in Scheme 5 and it relies on the hetero Diels Alder reaction between the in situ prepared heterodiene 17 and the protected L-fucal 3. Then, the cycloadduct 18 was in turn deprotected to obtain the fucose mimetic 10.

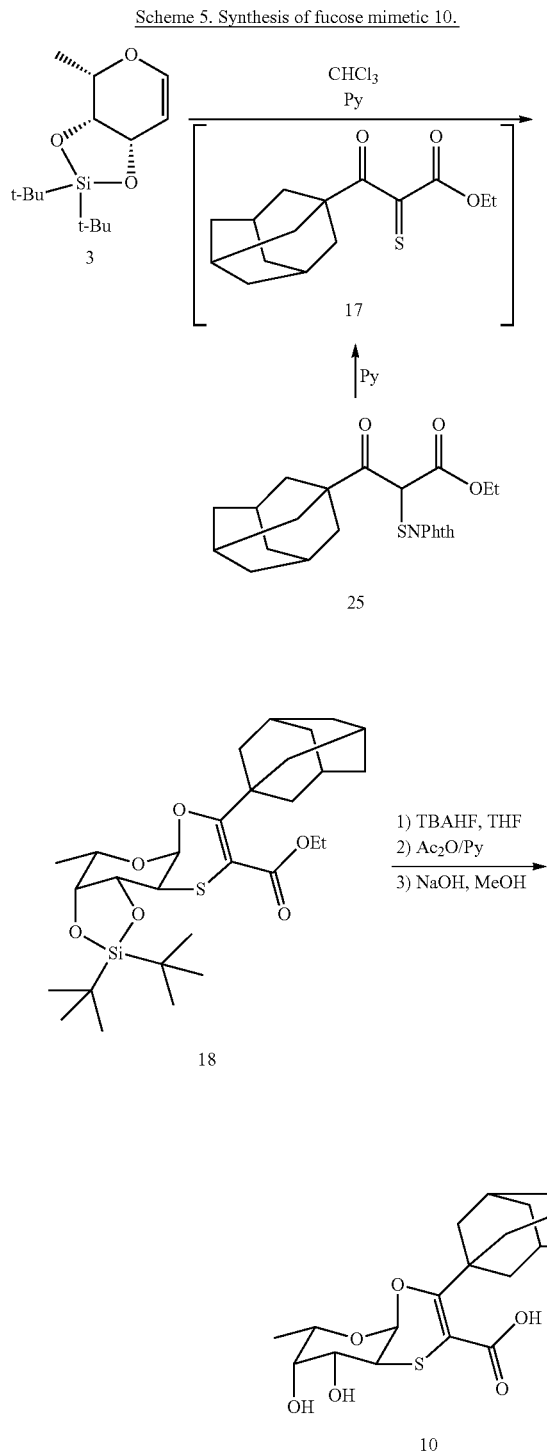

Scheme 5. Synthesis of fucose mimetic 10.

To synthesize compound 25 used in the synthesis of compound 10, to an ice-cooled solution of the commercially available ethyl 3-(1-adamantyl)-3-oxopropionate (1.0 g, 3.99 mmol) in CHCl$_3$, PhtNSC (0.765 g, 3.591 mmol) was added. The reaction mixture was stirred for 1 h then hexan was added and 1.3 g of a white solid was obtained.

To a stirred solution of 3 (100 mg, 0.37 mmol) in CHCl$_3$ (3.0 mL), 25 (423 mg, 0.877 mmol) and pyridine (300 uL, 3.7 mmol) were added. The reaction mixture was warmed at 45° C. and stirred for 96 h. Then, it was concentrated to dryness and the crude was purified by flash chromatography on silica gel (DCM: MeOH 15:1) to afford 134 mg of compound 18 (89% yield). To a stirred solution of 18 (70 mg, 0.13 mmol) a freshly prepared 1 M solution of TBAHF (1.04 mL) was added. The reaction mixture was stirred for 2 h at rt then, it was concentrated to dryness. This crude was dissolved in DCM (3.0 mL) and acetic anhydride (49 uL, 0.52 mmol) and pyridine (42 uL, 0.52 mmol) were added. The mixture was stirred at rt for 1 h then, it was diluted with DCM and washed with a saturated solution of NH$_4$Cl (2×20 mL) and with BRINE (2×20 mL). The organic phase was dried over Na$_2$SO$_4$, filtered and concentrated to dryness. The crude was purified by flash chromatography on silica gel (AcOEt:EP 1:6) to afford 16 mg of the protected intermediate 26.

Structure of the Intermediate Compound 26:

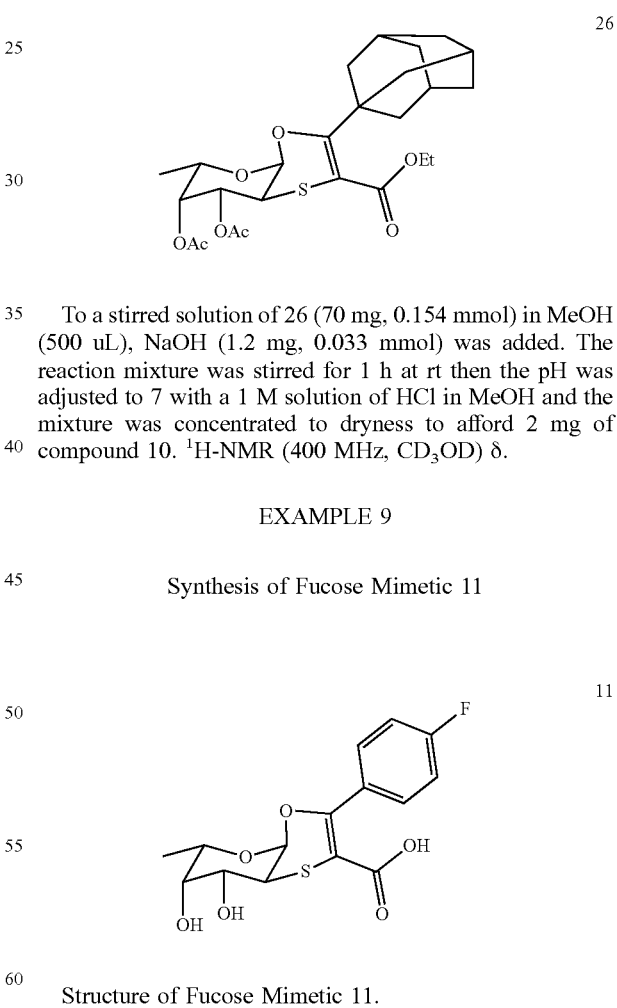

To a stirred solution of 26 (70 mg, 0.154 mmol) in MeOH (500 uL), NaOH (1.2 mg, 0.033 mmol) was added. The reaction mixture was stirred for 1 h at rt then the pH was adjusted to 7 with a 1 M solution of HCl in MeOH and the mixture was concentrated to dryness to afford 2 mg of compound 10. $^1$H-NMR (400 MHz, CD$_3$OD) δ.

EXAMPLE 9

Synthesis of Fucose Mimetic 11

Structure of Fucose Mimetic 11.

Fucose mimetic 11 has a structure which is related to the general structure E. The synthetic strategy is disclosed in Scheme 6 and it relies on the hetero Diels Alder reaction between the in situ prepared heterodiene 19 and the protected L-fucal 3. Then, the cycloadduct 20 was in turn deprotected to obtain the fucose mimetic 11.

Scheme 6. Synthesis of fucose mimetic 11.

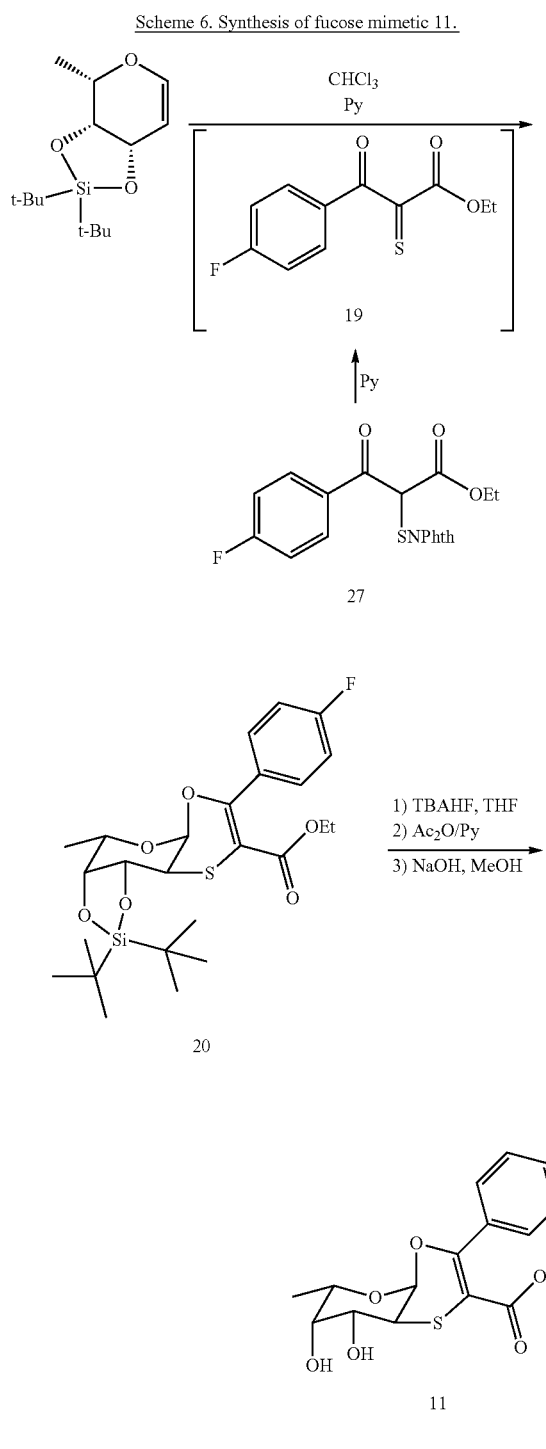

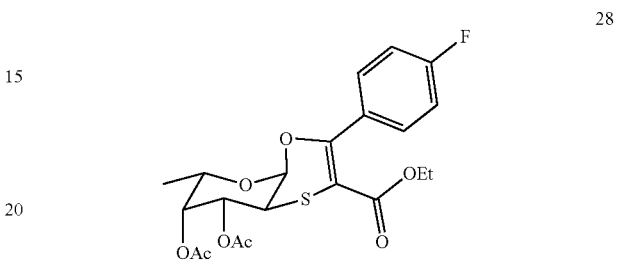

3.19 mmol) and pyridine (256 µL, 3.18 mmol) were added. The mixture was stirred at rt for 1 h then, it was diluted with DCM and washed with a saturated solution of $NH_4Cl$ (2×20 mL) and with BRINE (2×20 mL). The organic phase was dried over $Na_2SO_4$, filtered and concentrated to dryness. The crude was purified by flash chromatography on silica gel (AcOEt:EP 1:6) to afford 94 mg of the protected intermediate 28.

Structure of the Intermediate Compound 28:

To a stirred solution of 28 (70 mg, 0.154 mmol) in MeOH (500 uL), NaOH (37 mg, 0.92 mmol) was added. The reaction mixture was stirred for 1 h at rt then the pH was adjusted to 7 with a 1 M solution of HCl in MeOH and the mixture was concentrated to dryness to afford 50 mg of compound 11 (>98% yield). $^1$H-NMR (400 MHz, $CD_3OD$) δ: 7.42-7.35 (m, 2H), 7.11-7.03 (m, 2H), 5.72 (d, 1H, J=5.6 Hz, H-1), 4.13-4.03 (m, 1H, H-5), 3.78-3.69 (m, 2H, H-3, H-4), 3.47 (dd, J=10.5 Hz, 5.2 Hz, H-2), 1.22 (d, 3H, J=13.0 Hz, $CH_3$).

EXAMPLE 10

Multivalent Systems

Multivalent constructs containing the fucose mimetics of the invention either covalently or noncovalently linked are prepared. Specifically, the multivalent constructs can consist on, be part of, and/or are contained within organic/inorganic-based nanoparticles of different shape (i.e. sphere, rods, start, cubic, diamond, amorphous) and size (i.e. nm, µm) and include, but are not limited to, dendrimers, dendrons, polymeric nanomaterials and carbohydrate- or peptide/proteins or lipids- or nucleotide/nucleoside-based nanoparticles, liposomes, micelles, and gold or silver or silica or polyesters (i.e., polylactide, polycaprolactone and poly(lactic-co-glycolic acid)) nanoparticles, and viral or carbon-based (i.e., carbon nanotubes, graphene, carbon dots), external-stimuli responsive hydrogels.

Figure 8:
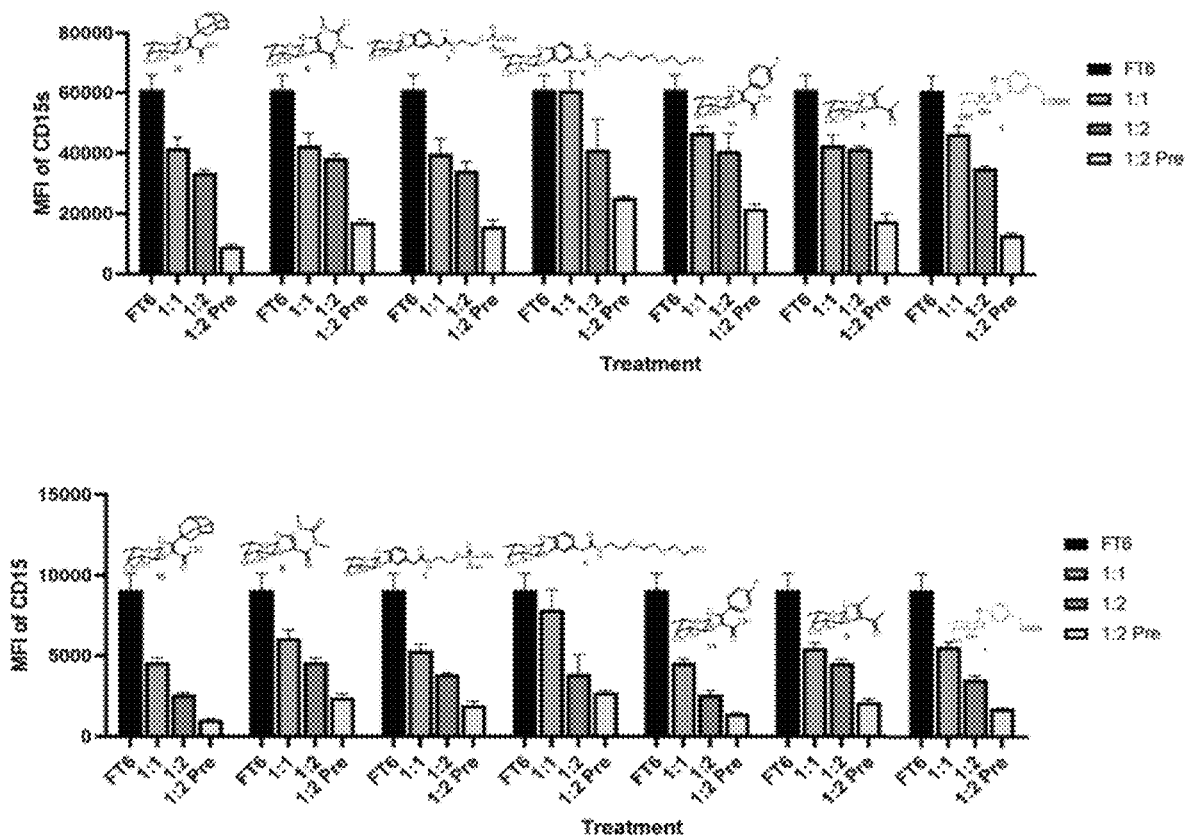
FIG. 8 shows FTVI exofucosylation inhibition of RPMI-8402 cells using seven different fucose mimetics (compounds 1, 5, 6, and 8-11) with the inhibition in the production of sLe$^X$ shown in the top row and the inhibition of Le$^X$ in the bottom row.
Figure 9:
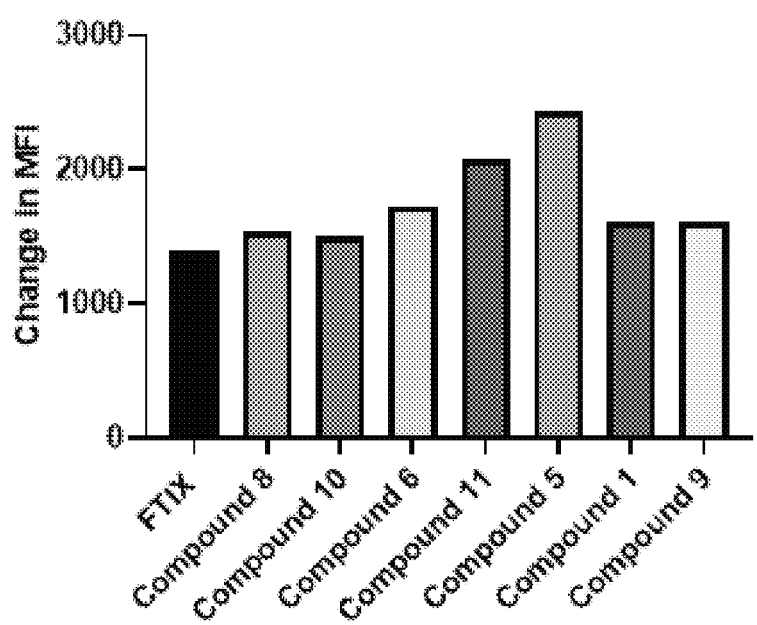
FIG. 9 shows FTIX exofucosylation inhibition of RPMI-8402 cells using seven different fucose mimetics (compounds 1, 5, 6, 8, 9, 10, and 11).

To a stirred solution of 3 (100 mg, 0.37 mmol) in $CHCl_3$ (3.0 mL), 27 (340 mg, 0.877 mmol) and pyridine (300 uL, 3.7 mmol) were added. The reaction mixture was warmed at 45° C. and stirred for 96 h. Then, it was concentrated to dryness and the crude was purified by flash chromatography on silica gel (DCM: MeOH 15:1) to afford 185 mg of compound 20 (⁓98% yield). To a stirred solution of 20 (182 mg, 0.356 mmol) a freshly prepared solution of TBAHF (2.85 mL) was added. The reaction mixture was stirred for 2 h at rt then, it was concentrated to dryness. This crude was dissolved in DCM (3.0 mL) and acetic anhydride (300 µL, For example, a multivalent system containing the fucose mimetic 1 was prepared. The synthesis of the hexavalent construct 32 was performed according to Bioconjugate Chem. 2018, 29, 83-88, the data of which are incorporated in its entirety herewith. The multivalent system containing the fucose mimetic 1 was synthesized according to Scheme 7. Specifically, cyclopeptide-based scaffolds were selected, which scaffolds have been proven useful for the construction of tetra-, hexa-, and hexadecavalent glycoconjugates. A cyclopeptide-based hexavalent structure (conjugate 32) displaying fucose mimetic 1 was synthesized (FIG. 8).

Scheme 7

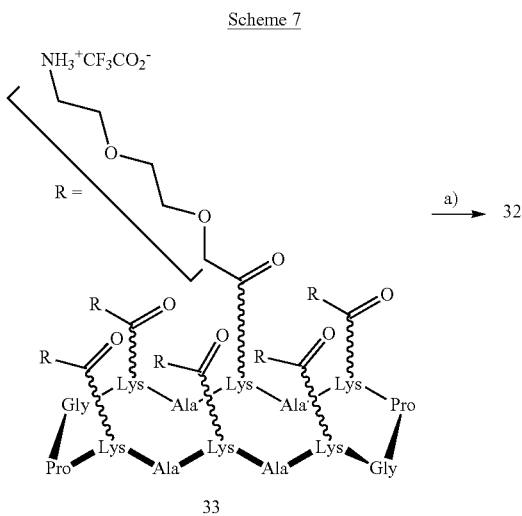

Hexavalent compound 32 was next prepared from scaffold 33 by PyBOP-promoted coupling with fucose mimetic 1 using DIPEA and DMF. The reaction occurred quantitatively at room temperature in 30 min and provided compound 32 in 50% yield after semipreparative high-performance liquid chromatography (HPLC) purification.

EXAMPLE 11

Bead-Conjugated Fucose Mimetic 7

Compound 7 was conjugated to Dynabeads™ M-270 Amine (ThermoFischer) using the following protocol. One hundred μL of a 10 mg/mL DMF solution of 7 were added to 500 μL of the beads dispersion. The dispersion was shaked for 30 min ar rt then the beads were washed with PBS pH 7.4 (3×10 mL) and bead-conjugated fucose mimetic 29 was obtained.

Scheme 8. Synthesis of magnetic beads conjugated to fucose mimetic 29.

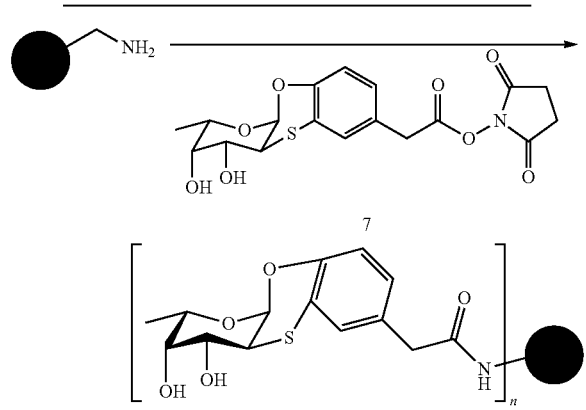

EXAMPLE 12

Inhibition of Fucosyltransferases

Exofucosylation is a technique whereby a pertinent FT together with GDP-Fuc is placed in a cell suspension to stereoselectively install fucose on pertinent acceptor cell surface glycan(s). For the case of α-1,3-FTs, this approach provides the ability to pinpoint the effect(s) of mimetic addition on creation of fucosylated glycans $Le^X$ and $sLe^X$, while keeping the rest of the cell's biological functions and its viability intact. Specifically, this study focused on three α-1,3-FTs that can create $sLe^X$ and $Le^X$ determinants: FTVII, FTIX, and FTVI. To assess enzymatic activity, two cell types were utilized, the human lymphoblastic leukemia cell line RPMI-8402 and human mesenchymal stem cells (MSCs). Each cell line was selected because these cell types do not natively express either $sLe^X$ or $Le^X$ determinants CD15s and CD15, respectively, but express both the sLacNAc and LacNAc acceptors.

Figure 1B:
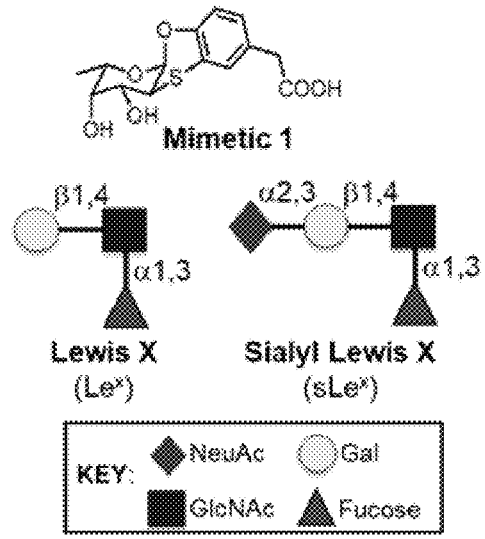
FIG. 1B shows a schematic representation of $Le^X$ and $sLe^X$.

Mimetic 1 (FIG. 1) was tested as an inhibitor of FT-mediated exofucosylation on these cells and the extent of fucosylation was monitored using antibodies that detect the creation of the relevant fucosylated epitopes, i.e., $sLe^X$ or $Le^X$. Cells were treated directly with reaction buffer containing the relevant FTs together with 1.0 mM GDP-Fuc and cells untreated with FTs (UT) were used as reference reaction negative control (FIG. 2A, 2B, 2C, FIG. 5 and FIGS. 6A and 6B).

Figures 2A, 2B, 2C:
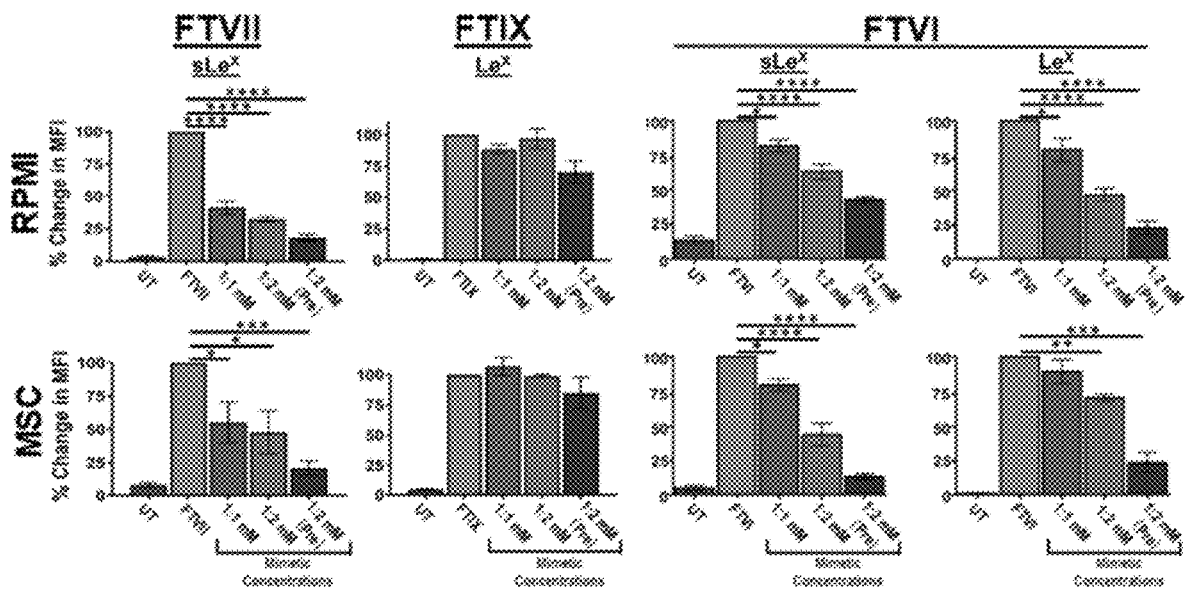
FIG. 2A shows percent changes in mean fluorescent intensity of RPMI-8402 cells (top row) and mesenchymal stem cells (MSC) (bottom row) treated with fucosyltransferase VII (FT VII) in the absence (red) or presence of 1.0 mM GDP-Fuc (orange); 1.0 mM GDP-Fuc and 1.0 mM mimetic 1 (blue); 1.0 mM GDP-Fuc and 2.0 mM mimetic 1 (light green) or after preincubation with FTVII and 2.0 mM mimetic 1 for 45 minutes followed by addition of 1.0 mM GDP-Fuc for 1 hour (dark green).
FIG. 2B shows percent changes in mean fluorescent intensity of RPMI-8402 cells (top row) and mesenchymal stem cells (MSC) (bottom row) treated with fucosyltransferase IX (FT XI) in the absence (red) or presence of 1.0 mM GDP-Fuc (orange); 1.0 mM GDP-Fuc and 1.0 mM mimetic 1 (blue); 1.0 mM GDP-Fuc and 2.0 mM mimetic 1 (light green) or after preincubation with FTIX and 2.0 mM mimetic 1 for 45 minutes followed by addition of 1.0 mM GDP-Fuc for 1 hour (dark green).
FIG. 2C shows percent changes in mean fluorescent intensity of RPMI-8402 cells (top row) and mesenchymal stem cells (MSC) (bottom row) treated with fucosyltransferase VI (FT VI) in the absence (red) or presence of 1.0 mM GDP-Fuc (orange); 1.0 mM GDP-Fuc and 1.0 mM mimetic 1 (blue); 1.0 mM GDP-Fuc and 2.0 mM mimetic 1 (light green) or after preincubation with FTVI and 2.0 mM mimetic 1 for 45 minutes followed by addition of 1.0 mM GDP-Fluc for 1 hour (dark green).
Figure 5A:
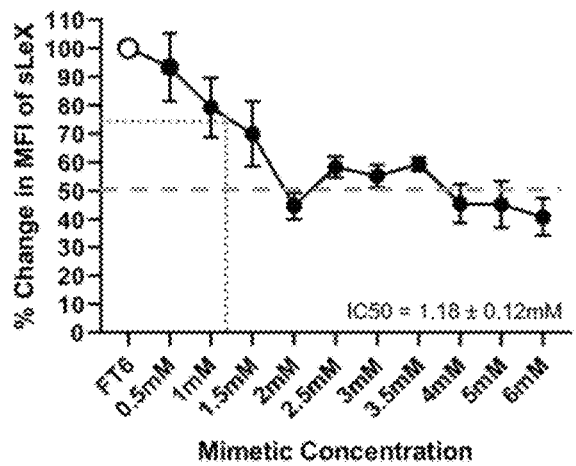
FIG. 5A shows the inhibition of exofucosylation of RPMI-8402 cells as percent change of mean fluorescence intensity of $sLe^X$ after incubation with FTVI in the presence of increasing concentrations of mimetic 1.
Figure 5B:
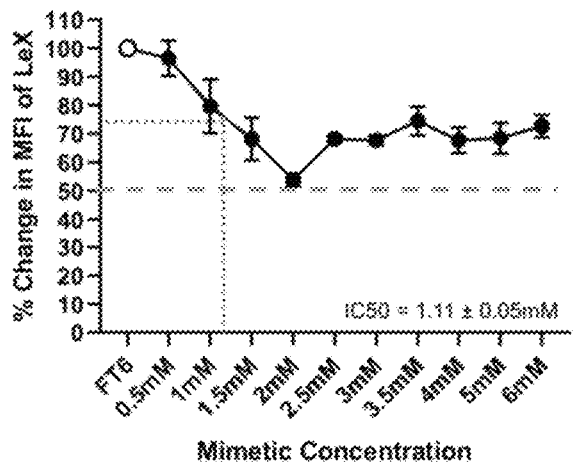
FIG. 5B shows the inhibition of exofucosylation of RPMI-8402 cells as percent change of mean fluorescence intensity of Le$^X$ after incubation with FTVI in the presence of increasing concentrations of mimetic 1.
Figure 5C:
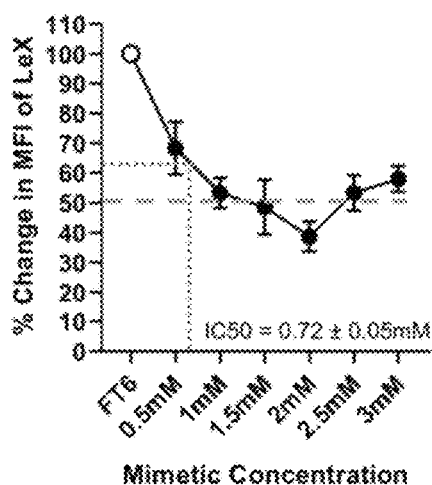
FIG. 5C shows the inhibition of exofucosylation of RPMI-8402 cells as percent change of mean fluorescence intensity of sLe$^X$ after incubation with FTVII in the presence of increasing concentrations of mimetic 1.
Figure 6A:
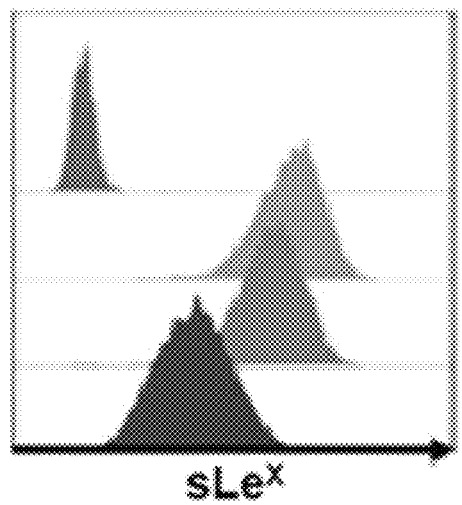
FIG. 6A shows mean fluorescence intensity of sLe$^X$ in untreated RPMI-8402 cells (red), RPMI-8402 cells exofucosylated with FTVI and 1.0 mM GDP-Fuc (orange), 1.0 mM GDP-Fuc and 2.0 mM mimetic 1 (light green), or preincubated with FTVI and 2.0 mM mimetic 1 for 45 minutes followed by addition of 1.0 mM GDP-Fuc for 1 hour (dark green).
Figure 6B:
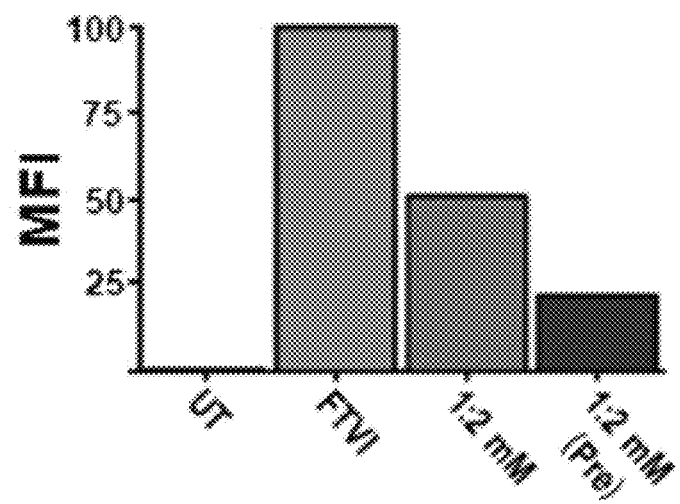
FIG. 6B shows the results of FIG. 8A as bar graph.
Figure 6C:
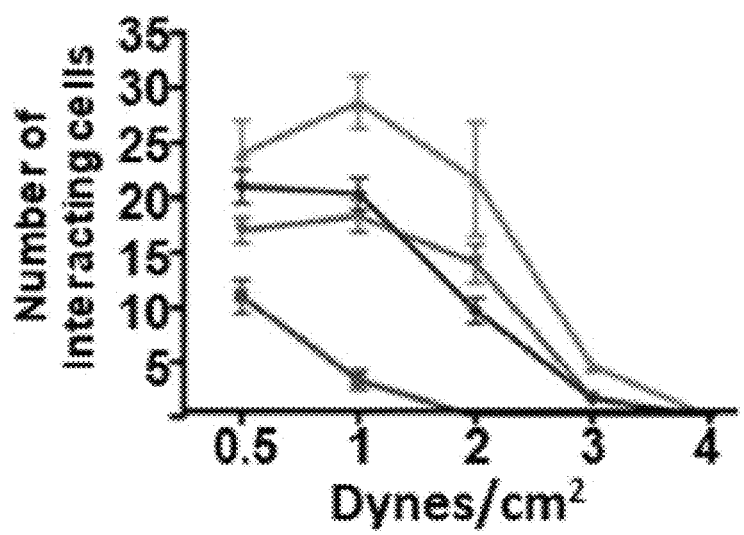
FIG. 6C shows the flow chamber results of RPMI-8402 cells treated as in FIG. 8A and loaded into flow chambers containing monolayers of E-selectin bearing HUVEC with an initial shear stress of 0.5 dyn/cm$^2$ and incremental increase up to 8 dynes/cm$^2$. The number of RPMI-8402 cell tethering/interactions were quantified at each shear rate and averaged across three different fields of view.

FTVI is capable of adding L-Fucose to both sialylated and neutral LacNAc acceptors (sLacNAc and LacNAc), whereas FTVII and FTIX hold strict specificity for sialylated (sLacNAc) and neutral type II LacNAc acceptors, respectively. In the first set of explorative experiments, it was sought to determine if mimetic 1 could inhibit production of $sLe^X$ on RPMI-8402 cells. Several reactions that contained either no enzyme (UT), FTVII with GDP-Fuc (1.0 mM) and then FTVII with two different concentrations of the mimetic 1 (1.0 mM and 2.0 mM, respectively) were performed. Moreover, a pre-incubation protocol was also analyzed, wherein the cell suspension was pre-treated with FTVII and a 2.0 mM solution of mimetic 1 followed by addition of 1.0 mM solution of GDP-Fuc (Pre). Results revealed that mimetic 1 was able to inhibit FTVII-driven $sLe^X$ expression on RPMI-8402 cells (FIG. 2A), with the degree of inhibition correlating with the increasing concentrations of mimetic 1. Notably, pre-incubation of FTVII with mimetic 1 provided a significant inhibition of $sLe^X$ production (FIG. 2A). To further test the specificity range of the mimetic 1 effect(s), exofucosylation was performed with FTIX (FIG. 2B). Unlike with FTVII, the results using RPMI-8402 cells indicated that mimetic 1 did not inhibit FTIX-mediated exofucosylation, i.e., had minimal effect on the creation of $Le^X$ (FIG. 2B). To assess whether these findings were cell/glycocalyx specific, a second cell type, MSCs, was employed because MSCs also display surface sLacNAc and LacNAc acceptors. FIGS. 2A and 2B are representative of exofucosylation reactions performed on MSCs using FTVII and FTIX under the same conditions used for RPMI-8402 cells. Again, FTVII inhibition was clear and proceeded stepwise with the addition of additional mimetic, and the levels of inhibition were stronger in the pre-incubation reactions. In contrast, and similar to results using RPMI-8402 cells, the mimetic did not inhibit FTIX production of $Le^X$. To determine if the selective inhibition of $sLe^X$ creation, but not $Le^X$ creation, was due to the ability of mimetic 1 to only interfere with FT-sLacNAc interactions, or if it was inherent to the inability of mimetic 1 to inhibit FTIX, the effects of the mimetic on FTVI activity were examined (FIG. 2C). It was found that unlike FTIX, FTVI production of $Le^X$ was clearly inhibited by mimetic 1 (FIG. 2C); yet like FTVII, the ability of FTVI to produce $sLe^X$ was also markedly diminished in both cell lines. Pre-incubation with the mimetic prior to addition of GDP-Fuc inhibited more completely exofucosylation reactions mediated by FTVI and FTVII but had no effect on FTIX, providing further evidence that mimetic 1 did not inhibit FTIX.

These differences between isoforms at the level of their inhibition could be a reflection of their discrete sequence identity (~40%) and indicated that their active sites or regions around were likely different. Two titration experiments were performed using FTVI and FTVII, respectively, 1.0 mM GDP-Fuc and different concentrations of mimetic 1 (FIGS. 7A and 7B) to determine the relative $IC_{50}$ value. Bell-shaped like concentration curves were obtained in the FTVI and in the FTVII reactions, which suggested the formation of colloidal aggregates at higher concentrations under the experimental conditions (>2.0 mM). The mimetic reached the highest inhibition at 2.0 mM against both FTVI and FTVII, with a slightly higher extent of inhibition on FTVII over FTVI (FIGS. 7A and 7B).

EXAMPLE 13

Shear Stress Experiments

As $sLe^x$ is the primary ligand for E-selectin which is induced on endothelial cells by inflammatory cytokine, e.g., TNFα the biological impacts of mimetic 1's inhibition of $sLe^x$ binding to E-selectin under hemodynamic shear was evaluated. To this end, RPMI-8402 cells were left untreated or exofucosylated with 1.0 mM GDP-Fuc, 1.0 mM GDP-Fuc and 2.0 mM mimetic 1 or preincubated with FTVI and 2.0 mM mimetic 1 for 45 min followed by addition of 1.0 mM GDP-Fuc for 1 h and the presence of $sLe^x$ determined by flow cytometry (FIGS. 8A and 8B). The RPMI-8402 cells treated as outlined above were then loaded in a parallel plate flow chamber seeded with monolayers of human umbilical vein endothelial cells (HUVEC) that had been stimulated with TNFα (FIG. 8C). The RPMI cells were introduced under defined fluid shear conditions to determine inhibition. Low shear conditions revealed that the binding interactions of integrins on all the treatment were intact as indicated by the number of interacting cells in the untreated group (FIG. 8C, red line). RPMI-84022 cells exofucosylated with FTVI and GDP-Fuc showed the highest number of interacting cells (FIG. 8C, orange line). In contrast, RPMI-8402 cells exofucosylated with FTVI in the presence of GDP-Fuc and mimetic 1 reduced the number of interacting cells (FIG. 8C, light green line); as did preincubation with FTVI and mimetic 1 followed by addition of GDP-Fuc (FIG. 8C, dark green line). These results demonstrated that mimetic 1 reduced the ability of cells to adhere to HUVEC under physiologically relevant shear conditions (FIG. 8C).

EXAMPLE 14

Lack of Effect on DC-Sign

Dendritic cell-specific intercellular adhesion molecule-3-grabbing non-integrin (DC-SIGN) is a human carbohydrate-binding protein, which belongs to the class of C-type lectins receptors (CLRs). It is primarily expressed on immature dendritic cells (DCs) and plays a key role in modulating immune responses. Specifically, recognition and internalization of carbohydrate-containing antigens by DCs is typically mediated by C-type lectin receptors and in particular by DC-SIGN. Natural ligands for DC-SIGN are high-mannose oligosaccharides and fucose-containing Lewis-type antigens.

Because the recognition of carbohydrate antigens is mediated by the carbohydrate recognition domain of DC-SIGN, nanomaterials that mimic physiological glycoproteins produced by a number of pathogens can be used as smart platforms to target DC-SIGN for the delivery of specific antigens in vaccine development.

Although mimetic 1 acts as an inhibitor of fucosylation, and also possesses the ability to bind pathogen (e.g., bacterial and fungal) associated fucose-binding lectins, the instant inventors discovered that fucose mimetic 1 was not recognized by the human fucose-binding DC-SIGN lectin. Therefore, unexpectedly, fucose mimetic 1 is able to inhibit human specific fucosyltransferases and, also unexpectedly, fucose mimetic 1 did not affect dendritic cells that play a key role in clearance of circulating 'non-self' constructs/entities via DC-SIGN.

Therefore, the fucose mimetics of the instant invention have surprising and highly beneficial functionalities that make them ideal therapeutic tools to target fucose-mediated interactions that are involved in disease processes in a subject while leaving unaffected the ability of a subject's circulating dendritic cells to clear 'non-self' constructs/entities via DC-SIGN.

EXAMPLE 15

Golgi Targeting

The fucose mimetics of the invention are functionalized with Golgi targeting modules to provide a specific targeting of the compounds to the selected organelle. In particular, Golgi targeting modules can be, but are not limited to, (D/L)-cysteine, mono-, di-, tri-thiols containing modules, fat acids modules with saturated and unsaturated alkyl chains, natural ceramide and related analogues, SNAP-Tag substrate, Halo-Tag substrate, sulphonamide derivatives, myristoyl-Gly-Cys module.

For example, the Golgi-targeting modules are covalently conjugated to the fucose mimetic scaffold. Therefore, any of the Golgi-targeting modules can be included in the R1-R7 groups or in the R'-R" groups or at the OH groups at the position C3 and C4 of the fucose moiety of the fucose mimetics of the invention. The covalent conjugation can be performed with or without an alkyl/aryl spacer which can be linked through a cleavable bond that is cleaved by specific stimuli, e.g., pH, enzyme, light, and/or temperature or through a stable bond. The Golgi-targeting modules can be included in drug delivery systems as described in 'Pharmaceutical Formulations and Routes of Administration' which can be, but are not limited to, organic and inorganic nanoparticles, nanomaterials, liposomes, micelles, hydrogels, micro- or nano-spheres, mesoporous materials, dendrimers, dendrons.

We claim:

1. A fucose mimetic compound having Structure A and/or a therapeutically effective salt thereof, wherein the dotted line is an aliphatic, an aromatic, a heteroaliphatic, or a heteroaromatic ring and is substituted with at least one $R^1$, wherein the ring can be substituted with any number of $R^1$ substituents up to the maximum number permitted by the structure of the ring, and n is an integer selected from the group consisting of 2, 3, 4, 5, 6, 7 and 8;

wherein at each occurrence R is hydrogen or a group selected from hydroxyl, alkoxy, amino, thiol, sulfoxide, sulfone, sulfonamide, sulphate, sulfonate, keto, formyl, carboxylic, azido, (mono-, di, tri-) phosphate, (mono-, di-, tri-) phosphonate, ester, amide, and anhydride wherein said group further comprises a protecting group, wherein the protecting group can form an ester with the adjacent oxygen atom or is independently selected from (D/L)-cysteine, a mono-, di-, tri-thiol containing molecule, a fat acid with saturated and unsaturated alkyl chains, a natural ceramide, a sulphonamide, and a myristoyl-Gly-Cys molecule;

wherein at each occurrence $R^1$ is independently selected from substituted or unsubstituted alkyl, substituted or unsubstituted heteroalkyl, substituted or unsubstituted aryl, substituted or unsubstituted heteroaryl, substituted or unsubstituted alkyl-aryl, a substituted or unsubstituted polycyclic group, amino, thiol, sulfide, keto, formyl, carboxyl, azide, phosphyl, ester, amide, and anhydride; wherein the substituents are selected from keto, amino, phosphate, halogen, hydroxyl, nitro, alkyl, alkenyl, aryl, formyl, and acetyl;

wherein X and Y are independently $CH_2$, S, S=O, $SO_2$, O, or NH; $R^2$ is $CH_2R''$, $CH_2OR''$, $CH_2N(R'')_2$, or $CH_2SR''$; R'' is selected from the group consisting of hydrogen, hydroxyl, amino, thiol, sulfide, keto, formyl, carboxyl, azide, (mono-, di-, tri-) phosphate, (mono-, di-, tri-) phosphonate, substituted or unsubstituted alkyl, substituted or unsubstituted heteroalkyl, substituted or unsubstituted aryl, and substituted or unsubstituted heteroaryl; and X' is C, S, S=O, $SO_2$, O, or N.

2. The fucose mimetic compound according to claim 1 having Structure B

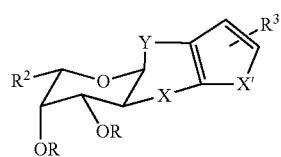

wherein the five member cycle is substituted with up to four $R^3$ substituents; wherein each $R^3$ is selected from hydrogen, hydroxyl, substituted or unsubstituted alkyl, substituted or unsubstituted heteroalkyl, substituted or unsubstituted aryl, substituted or unsubstituted heteroaryl, substituted or unsubstituted alkyl-aryl, amino, thiol, sulfide, keto, formyl, carboxyl, azide, ester, amide, and anhydride thereof; X' is C, S, S=O, $SO_2$, O, or N; and wherein X' can be present in any position of the five member cycle.

3. The fucose mimetic compound according to claim 1 having Structure C

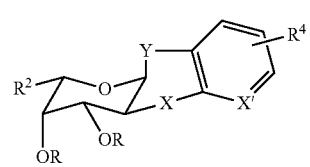

wherein the six member cycle is substituted with up to four $R^4$ substituents wherein each $R^4$ is selected from substituted or unsubstituted alkyl, substituted or unsubstituted heteroalkyl, substituted or unsubstituted aryl, substituted or unsubstituted heteroaryl, substituted or unsubstituted alkyl-aryl, amino, thiol, sulfide, keto, formyl, carboxyl, azide, ester, amide, and anhydride, wherein the substituents are selected from keto, amino, phosphate, halogen, hydroxyl, nitro, alkyl, alkenyl, aryl, formyl, and acetyl; and X' is C, S, S=O, $SO_2$, O, or N.

4. The fucose mimetic compound according to claim 1 having Structure D

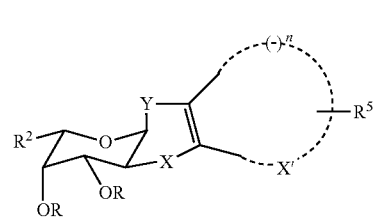

wherein the dotted line is an aliphatic or heteroaliphatic ring substituted with up to twelve $R^5$ substituents; n is an integer selected from the group consisting of 2, 3, 4, 5, and 6; X' is C, S, S=O, $SO_2$, O, or N; wherein each $R^5$ is selected from hydrogen, hydroxyl, substituted or unsubstituted alkyl, substituted or unsubstituted heteroalkyl, substituted or unsubstituted aryl, substituted or unsubstituted heteroaryl, substituted or unsubstituted alkyl-aryl, amino, thiol, sulfide, keto, formyl, carboxyl, azide, ester, amide, and anhydride; and wherein X' can be present in any position of the aliphatic or heteraliphatic ring.

5. A fucose mimetic compound having Structure E

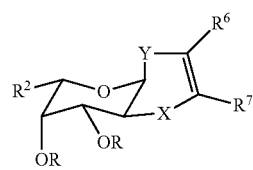

and/or a therapeutically effective salt thereof, wherein:
X and Y each independently are selected from $CH_2$, S, S=O, $SO_2$, O, or NH;
$R^2$ is selected from $CH_2R''$, $CH_2OR''$, $CH_2N(R'')_2$, or $CH_2SR''$; R'' is selected from hydrogen, hydroxyl, amino, thiol, sulfide, keto, formyl, carboxyl, (mono-, di-, tri-) phosphate, (mono-, di-, tri-) phosphonate group, substituted or unsubstituted alkyl, substituted or unsubstituted heteroalkyl, substituted or unsubstituted aryl, and substituted or unsubstituted heteroaryl;

$R^6$ is selected from hydrogen, hydroxyl, substituted or unsubstituted alkyl, substituted or unsubstituted heteroalkyl, substituted or unsubstituted aryl, substituted or unsubstituted heteroaryl, substituted or unsubstituted alkyl-aryl, substituted or unsubstituted polycyclic group, amino, thiol, sulfide, keto, formyl, carboxyl, azide, phosphyl, ester, amide, and anhydride; wherein the substituents are selected from halogen, hydroxyl, alkoxy, nitro, alkyl, alkenyl, aryl, formyl, acetyl;

$R^7$ is selected from hydrogen, substituted or unsubstituted alkyl, substituted or unsubstituted heteroalkyl, substituted or unsubstituted aryl, substituted or unsubstituted heteroaryl, substituted or unsubstituted alkyl-aryl, substituted or unsubstituted polycyclic group, amino, thiol, sulfide, keto, formyl, carboxyl, azide, phosphyl, ester, amide, and anhydride; wherein the substituents are selected from halogen, hydroxyl, alkoxy, nitro, alkyl, alkenyl, aryl, formyl, acetyl; and R is independently selected from hydrogen, (D/L)-cysteine, a mono-, di-, tri-thiol containing molecule, a fat acid with saturated and unsaturated alkyl chains, a natural ceramide, a sulphonamide, and a myristoyl-Gly-Cys molecule, or R can form an ester with the adjacent oxygen atom.

6. A composition comprising the fucose mimetic compound and/or a multivalent system containing the fucose mimetic compound according to claim 1.

7. The composition according to claim 6 comprising a therapeutically effective amount of

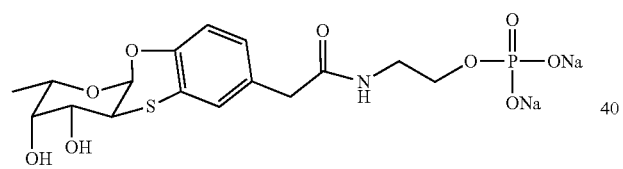

5 and a pharmaceutically acceptable carrier.

8. The composition according to claim 6 comprising a therapeutically effective amount of

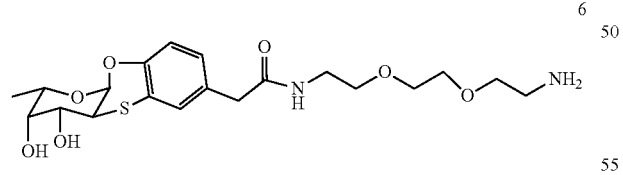

6 and a pharmaceutically acceptable carrier.

9. A composition comprising the fucose mimetic compound and/or a multivalent system containing the fucose mimetic compound according to claim 5, wherein the compound is compound 9

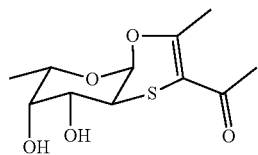

9 and a pharmaceutically acceptable carrier.

10. A composition comprising the fucose mimetic compound and/or a multivalent system containing the fucose mimetic compound according to claim 5, wherein the compound is compound 10

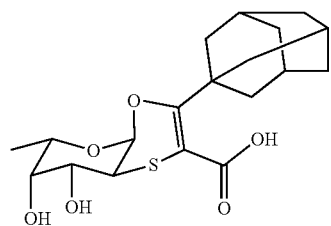

10 and a pharmaceutically acceptable carrier.

11. A composition comprising the fucose mimetic compound and/or a multivalent system containing the fucose mimetic compound according to claim 5, wherein the compound is

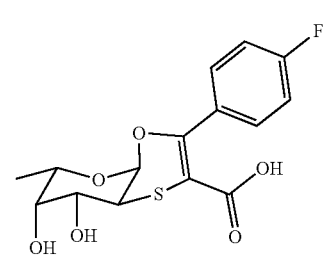

11 and a pharmaceutically acceptable carrier.

12. The fucose mimetic compound of claim 5, wherein R is independently selected from hydrogen, (D/L)-cysteine, a fat acid with saturated and unsaturated alkyl chains, a natural ceramide, and a sulphonamide, or R can form an ester with the adjacent oxygen atom.

* * * * *